United States Patent [19]

Cook et al.

[11] Patent Number: 5,514,786
[45] Date of Patent: May 7, 1996

[54] COMPOSITIONS FOR INHIBITING RNA ACTIVITY

[75] Inventors: Phillip D. Cook; Thomas Bruice; Charles J. Guinosso, all of Carlsbad; Andrew M. Kawasaki, Oceanside, all of Calif.

[73] Assignee: Isis Pharmaceuticals, Inc., Carlsbad, Calif.

[21] Appl. No.: 942,961

[22] Filed: Sep. 10, 1992

Related U.S. Application Data

[63] Continuation-in-part of Ser. No. 846,556, Mar. 5, 1992, Pat. No. 5,359,051, which is a continuation-in-part of PCT/US91/00243, Jan. 11, 1991, which is a continuation-in-part of Ser. No. 463,358, Jan. 11, 1990, abandoned, and a continuation-in-part of Ser. No. 566,977, Aug. 13, 1990, abandoned.

[51] Int. Cl.$^6$ ............................. C07H 21/00; C12Q 1/68; A61K 48/00
[52] U.S. Cl. ............................................. 536/23.1; 435/6
[58] Field of Search ............................. 536/23.1; 514/44; 435/6

[56] References Cited

FOREIGN PATENT DOCUMENTS

| | | |
|---|---|---|
| 0214908 | 3/1987 | European Pat. Off. . |
| 0260032 | 8/1987 | European Pat. Off. . |
| WO91/15499 | 10/1991 | WIPO . |

OTHER PUBLICATIONS

Hélène, C. et al. Control of gene expression by oligonucleotides covalently linked to intercalating agents. Genome (1989) 31:413–421.
European Patent 214908 issued to CNRS published Mar. 18, 1987. (Abstract).
Hélène, C. et al. Sequence specific artificial endonucleases. Trends Biotech. (1989) 7:310–315.
Luo, F. T., et al. Palladium–catalyzed cyclization and cross–coupling of acetylenic aryltrifutes with organotin reagents. Tetrahedron Letters (1991) 32:7703–7706(Abs).
Breslow, R., et al. Ribonucleas urimes. Tetrahedron (1991) 47:2365–2376.
Bashkin et al. Synthesis and characterization of nucleoside peptides: Toward chemical ribonucleases. J. Org. Chem (1990) 55:5125–5132.
Stein et al. Antisense Oligonucleotides as Therapeutic Agents–Is the Bullet Really Magical? Science (Aug 20, 1993) 261:1004–1012.
Stein et al., "Oligodeoxynucleotides as Inhibitors of Gene Expression: A Review", Cancer Research, 48:2659–2668 (1988).
Marcus–Sekura, Review, "Techniques for Using Antisense Oligodeoxyribonucleotides", Anal. Biochemistry, 172:289–295 (1988).
Zon, "Synthesis of Backbone–Modified DNA Analogues for Biological Applications", Journal of Protein Chemistry, 6:131–145 (1987).
Zon, "Oligonucleotide Analogues as Potential Chemotherapeutic Agents", Pharmaceutical Research, 5:539–549 (1988).

Van der Krol et al., "Modulation of Eukaryotic Gene Expression By Complementary RNA or DNA Sequences", BioTechniques, 6:958–973 (1988).
Loose–Mitchell, "Antisense nucleic acids as a potential class of pharmaceutical agents", TIPS, 9:45–47 (1988).
Cazenave et al., "Enzymatic amplification of translation inhibition of rabbit β–globin mRNA mediated by anti–messenger oligodeoxynucleotides covalently linked to intercalating agents", Nucleic Acids Research, 15:4717–4736 (1987).
Constant et al., "Hetrodimeric Molecules Including Nucleic Acid Bases and 9–Aminoacridine Spectroscopic Studies, Conformations, and Interactions with DNA", Biochemistry, 27:3997–4003 (1988).
Yeung et al., "Photoreactivities and Thermal Properties of Psoralen Cross–Links", Biochemistry, 27:2304–3210 (1988).
Meyer et al., "Efficient, Specific Cross–Linking and Cleavage of DNA by Stable, Synthetic Complementary Oligodeoxynucleotides", J. Am. Chem. Soc., 111:8517–8519 (1989).
Knorre et al., Progress in Nucleic Acid Research and Molecular Biology, 32:291–320 (1985).
Le Doan et al., "Sequence–targeted chemical modifications of nucleic acids by complementary oligonucleotides colatently linked to porphyrins", Nucleic Acids Research, 15:8643–8659 (1987).
Sigman, "Nuclease Activity of 1,10–Phenanthroline–Copper Ion", Acc.Chem.Res., 19:180–186 (1986).
Dreyer et al., "Sequence–specific cleavage of single–stranded DNA: Oligodeoxynucleotide–EDTA–Fe(II)", Proc. Natl. Acad. Sci. USA, 82:968–972 (1985).
Caruthers, "Synthesis of Oligonucleotides and Oligonucleotide Analogues", Oligonucleotides. Antisense Inhibitors of Gene Expression., pp. 7–24, J. S. Cohen, ed. (CRC Press, Inc. Boca Raton, Florida, 1989).
Beaucage et al., "Deoxynucleoside Phosphormidites—A New Class of Key Intermediates for Deoxypolynucleotide Synthesis", Tetrahedron Letters, 22:1859–1862 (1981).
Helene et al., Sequence–specific artificial endonucleases, Trends Biotech., 7:310–315, Nov. 1989.
Helene et al., Control of gene expression by oligonucleotides covalently linked to intercalating agents, Antisense RNA, 31:413–421, 1989.

(List continued on next page.)

Primary Examiner—W. Gary Jones
Assistant Examiner—David Schreiber
Attorney, Agent, or Firm—Woodcock Washburn Kurtz Mackiewicz & Norris

[57] ABSTRACT

Compositions and methods for modulating the activity of RNA are disclosed. In accordance with preferred embodiments, antisense compositions are prepared comprising targeting and reactive portions. The reactive portions preferably comprise one or two imidazole functionalities conjugated to the targeting oligonucleotide via linkers with or without intervening intercalating moieties. Therapeutics, diagnostics and research methods also are disclosed, as are synthetic nucleosides and nucleoside fragments that can be elaborated into oligonucleotides.

21 Claims, 8 Drawing Sheets

OTHER PUBLICATIONS

Gait, et al., "Solid–phase Synthesis of Oligodeoxyribonucleotides by the Phosphitetriester Method", *Oligonucleotide Synthesis, a practical approach*, 1985, 35–79.

Iribarren, et al., "2' –O –Alkyl oligoribonucleotides as antisense probes", *Proc. Natl. Acad. Sco., USA*, 87, 1990, 7747–7751.

Sproat, et al., "New synthetic routes to synthons suitable for 2' –O–allyloligoribonucleotide assembly", *Nucleic Acids Research*, 19, 1991, 733–738.

Walder, "Antisense DNA and RNA: progress and prospects", *Genes & Development*, 2, 1988, 502–504.

18 cis,cis
19 trans, trans

COMPOSITIONS FOR INHIBITING RNA ACTIVITY

RELATED APPLICATIONS

This application is a continuation-in-part of application Ser. No. 846,556, filed Mar. 5, 1992, issued as U.S. Pat. No. 5,359,051, which is a continuation-in-part of application Ser. PCT US91/00243, filed Jan. 11, 1991, which is a continuation-in-part of application Ser. No. 463,358, filed Jan. 11, 1990, abandoned, and application Ser. No. 566,977, filed Aug. 13, 1990, abandoned. These applications are assigned to the assignee of this invention. The entire disclosure of each is incorporated herein by reference.

FIELD OF THE INVENTION

This invention relates to materials and methods for detecting and modulating the activity of RNA. The invention generally relates to the field of "antisense" compounds which are capable of specific hybridization with a nucleotide sequence of an RNA. In accordance with preferred embodiments, this invention is directed to the design, synthesis, and application of oligonucleotides and to methods for achieving therapeutic treatment of disease, regulating gene expression in experimental systems, assaying for RNA and for RNA products through the employment of antisense interactions with such RNA, diagnosing diseases, modulating the production of proteins, and cleaving RNA in a site specific fashion.

BACKGROUND OF THE INVENTION

It is well known that most of the bodily states in mammals, including most disease states, are effected by proteins. Such proteins, either acting directly or through their enzymatic or other functions, contribute in major proportion to many diseases in animals and man. Classical therapeutics has generally focused upon interactions with such proteins in efforts to moderate their disease-causing or disease-potentiating functions. Recently, however, attempts have been made to modulate the actual production of such proteins by interactions with the intracellular RNA molecules that code for their synthesis. By interfering with the production of proteins, it has been hoped to effect therapeutic results with maximum effect and minimal side effects. It is the general object of such therapeutic approaches to interfere with or otherwise modulate gene expression which would lead to undesired protein formation.

One method for inhibiting specific gene expression is the use of oligonucleotides as "antisense" agents. The oligonucleotides complementary to a specific target messenger RNA (mRNA) sequence are used. A number of workers have reported such attempts. Pertinent reviews include Stein, et al., *Cancer Research* 1988, 48, 2659; Walder, *Genes & Development* 1988, 2, 502; Marcus-Sekura, *Anal. Biochemistry* 1988, 172, 289; Zon, *Journal of Protein Chemistry* 1987, 6, 131; Zon, *Pharmaceutical Research* 1988, 5, 539; Van der Krol, et al., *BioTechniques* 1988, 6, 958; and Loose-Mitchell, *TIPS* 1988, 9, 45. Each of the foregoing provide background concerning general antisense theory and prior techniques.

Thus, antisense methodology has been directed to the complementary hybridization of relatively short oligonucleotides to single-stranded mRNA or single-stranded DNA such that the normal, essential functions of these intracellular nucleic acids are disrupted. Hybridization is the sequence specific hydrogen bonding of oligonucleotides via Watson-Crick base pairs to RNA or single-stranded DNA. The bases of such base pairs are said to be complementary to one another.

Prior attempts at antisense therapy have provided oligonucleotides which are designed to bind in a specific fashion to—i.e., which are specifically hybridizable with— a specific mRNA by hybridization. Such analogs are intended to inhibit the activity of the selected mRNA—e.g., to interfere with translation reactions by which proteins coded by the mRNA are produced—by any of a number of mechanisms. It has been hoped to provide therapeutic benefits by inhibiting the formation of the specific proteins which are coded for by the mRNA sequences.

A number of chemical modifications have been introduced into antisense oligonucleotides to increase their therapeutic activity. Such modifications are designed to increase cell penetration of the antisense oligonucleotides, to stabilize them from nucleases and other enzymes that degrade or interfere with the structure or activity of the oligonucleotides in the body, to enhance their binding to targeted RNA, to provide a mode of disruption (terminating event) once sequence-specifically bound to targeted RNA, and to improve their pharmacokinetic properties. At present, however, no generalized antisense oligonucleotide therapeutic or diagnostic scheme has been found. The most serious deficiency of prior efforts has been the complete lack of a termination event once appropriate hybridization takes place or the occurrence of a termination event that is so inefficient that a useful potency cannot be achieved due to the inability of oligonucleotides to be taken into cells at effective concentrations. The activity of the antisense oligonucleotides presently available has not been sufficient for effective therapeutic, research reagent, or diagnostic use in any practical sense. Accordingly, there has been and continues to be a long-felt need for oligonucleotides which are capable of effective therapeutic and diagnostic antisense use.

This long-felt need has not been satisfied by prior work in the field of antisense oligonucleotide therapy and diagnostics. Others have failed to provide materials which are, at once, therapeutically or diagnostically effective at reasonable concentrations.

Initially, only two mechanisms or terminating events have been thought to operate in the antisense approach to therapeutics. These are the "hybridization arrest" mechanism (i.e., arrest of translation via antisense hybridization) and the cleavage of hybridized RNA by the cellular enzyme, ribonuclease H (RNase H). It is likely that additional "natural" events may be involved in the disruption of targeted RNA, however. Other terminating events also have been studied in an attempt to increase the potency of oligonucleotides for use in antisense diagnostics and therapeutics. Thus, an area of research has developed in which a second domain of the oligonucleotide, generally referred to as a pendant group, has been introduced.

The pendant group is not involved with the specific Watson-Crick hybridization of the oligonucleotide with the mRNA but is carried along by the oligonucleotide to serve as a reactive functionality. The pendant group is intended to interact with the mRNA in some manner to more effectively inhibit translation of the mRNA into protein. Such pendant groups have also been attached to molecules targeted to either single or double stranded DNA.

The type of pendant group known as an intercalating agent has been disclosed by Cazenave, et al., *Nucleic Acid Research* 1987, 15, 4717 and Constant, et al., *Biochemistry* 1988, 27, 3997. The disclosed purpose of such intercalating agents is to add binding stability to the hybrid formed between the oligonucleotide and the target nucleic acid by binding to the duplex formed between them.

It has also been disclosed to provide a pendant group to oligonucleotides which is capable of cross-linking. Thus, a pendant agent such as psoralen has been disclosed by Yeung, et al., *Biochemistry* 1988, 27, 2304. It is believed that after hybridization of the oligonucleotide to the target mRNA, the psoralen is photoactivated to cross-link with the mRNA forming a covalent bond between the oligonucleotide and the mRNA, thereby permanently inactivating the mRNA molecule and precluding the further formation of protein encoded by that particular portion of RNA.

It has also been proposed to employ a cross-linking alkylating agent as a pendant group for oligonucleotides for use in antisense approaches to diagnostics and therapeutics, as disclosed by Meyer, *J. Am. Chem. Soc.* 1989, 111, 8517 and Knorre and Vlassov, *Progress in Nucleic Acid Research and Molecular Biology* 1985, 32, 291.

The object of employing alkylating agents as pendant groups in oligonucleotides in antisense approaches is to cause the alkylating agent to react irreversibly with the target mRNA. Such irreversible binding between the antisense oligonucleotide and the mRNA is generally covalent and leads to permanent inactivation of the mRNA with a concomitant halt in protein production from the portion of mRNA thus inactivated.

A further strategy which has been proposed is to use chemical reagents which, under selected conditions, can generate a radical species for reaction with the target nucleic acid to cause cleavage or otherwise to inactivate it. Proposed pendant groups of this category include coordination complexes containing a metal ion with associated ligands. A metal ion can change oxidation state to generate reactive oxygen-containing radical ions or other radical species. Doan, et al, *Nucleic Acids Research* 1987, 15, 8643 have disclosed iron/EDTA and iron/porphyrin species for this purpose. Copper/phenanthroline complexes have been disclosed by Sigman, *Accounts of Chemical Research* 1986, 19, 180. Dreyer, et al., *Proceedings of the National Academy of Sciences, U.S.A.* 1985, 82, 968 have investigated the EDTA/Fe moiety to cleave nucleic acids.

Prior approaches using cross-linking agents, alkylating agents, and radical-generating species as pendant groups on oligonucleotides for antisense diagnostics and therapeutics have several significant shortcomings. The sites of attachment of the pendant groups to oligonucleotides play an important, yet imperfectly known, part in the effectiveness of oligonucleotides for therapeutics and diagnostics. Prior workers have described most pendant groups as being attached to a phosphorus atom which, as noted above, affords oligonucleotides with inferior hybridization properties. Prior attempts have been relatively insensitive in that the reactive pendant groups have not been effectively delivered to sites on the messenger RNA molecules for alkylation or cleavage in an effective proportion. Moreover, even if the reactivity of such materials were perfect, i.e. if each reactive functionality were to actually react with a messenger RNA molecule, the effect would be no better than stoichiometric. That is, only one mRNA molecule would be inactivated for each molecule of oligonucleotide. It is also likely that the non-specific interactions of the modified oligonucleotides with molecules other than the target RNA, for example with other molecules that may be alkylated or which may react with radical species, as well as possible self-destruction of the oligonucleotides, not only diminishes the diagnostic or therapeutic effect of the antisense treatment but also leads to undesired toxic reactions in the cell or in vitro. This is especially acute with the radical species which are believed to be able to diffuse beyond the locus of the specific hybridization to cause undesired damage to non-target materials, other cellular molecules, and cellular metabolites. This perceived lack of specificity and stoichiometric limit to the efficacy of such prior alkylating agent and radical generating-types of antisense oligonucleotides is a significant drawback to their employment.

Accordingly, there remains a great need for antisense oligonucleotide formulations which are capable of improved specificity and effectiveness both in binding and in mRNA modulation or inactivation without the imposition of undesirable side effects.

OBJECTS OF THE INVENTION

It is one object of this invention to provide oligonucleotides for use in antisense oligonucleotide diagnostics and therapeutics.

It is a further object of this invention to provide such oligonucleotides which are effective in modulating the activity of an RNA.

A further object of this invention is to provide such oligonucleotides which are less likely to evoke undesired or toxic side reactions.

A further object is to provide research and diagnostic methods and materials for assaying bodily states in animals, especially diseased states.

A further object is to provide means for modifying nucleic acids for effecting substitutions on selective portions thereof.

Yet another object is to provide therapeutic and research methods and materials for the treatment of diseases through modulation of the activity of DNA and RNA.

Still another object is to provide means for the selective cleavage of RNA.

These and other objects will become apparent to persons of ordinary skill in the art from a review of the present specification and appended claims.

SUMMARY OF THE INVENTION

In accordance with the present invention, compositions for modulating the activity of DNA and RNA are provided. The compositions useful for modulating the activity of an RNA or detecting its presence in accordance with this invention generally comprise three portions. The first portion, the targeting portion, is a portion which is specifically hybridizable with a preselected nucleotide sequence of the RNA. The compositions further comprise intercalating portions capable of intercalating between base pairs formed upon hybridization with RNA. The compositions further comprise a reactive portion capable of catalyzing or otherwise effecting the cleavage of RNA, especially of its phosphodiester bonds. Preferred compositions according to the present invention comprise at least one ribofuranosyl unit which bears at its 2' position both an intercalating portion and a reactive portion. The compositions may also include a tether or some other means for connecting the targeting and reactive portions together to form the composition.

The targeting portion of the compositions of this invention preferably comprises an oligonucleotide including from about 3 to about 50 base units with 8 to 40 subunits being preferred and 12 to 25 being still more preferred. Oligonucleotides having about 15 base units are preferable for the practice of certain embodiments of the present invention. Preferably, the targeting portion is an analog of an oligonucleotide wherein at least some of the phosphodiester bonds of the oligonucleotide have been substituted with a structure which functions to enhance nuclease resistance and/or to enhance the ability of the compositions to penetrate into the intracellular region of cells where the RNA whose activity is to be modulated is located. It is preferred that such substitutions comprise phosphorothioate bonds or short chain alkyl or cycloalkyl structures. In accordance with other preferred embodiments, the phosphodiester bonds are substituted with structures which are, at once, substantially non-ionic and non-chiral.

In certain preferred embodiments, the intercalating portions of the compositions are known, non-carcinogenic types of polycyclic aromatic hydrocarbons or heterocyclic moieties capable of intercalating between predetermined base pairs formed by a hybrid antisense/RNA target sequence duplex.

In accordance with other preferred embodiments the reactive portion of the composition comprises a functionality capable of catalyzing the hydrolysis or cleavage of phosphodiester bonds in RNA. Such functionalities may either be basic, acidic, amphoteric, ionic, or hydrophobic. Heteroatomic species can be formulated to be either basic or acidic or, indeed, to be amphoteric for such purposes.

This invention also comprehends the employment of alkylating and free-radical-forming functionalities as the reactive portions of the subject compositions, particularly where said alkylating or free-radical-forming materials are delivered into the minor groove of the hybrid formed between the compositions of the invention and the RNA to be modulated.

In accordance with other embodiments, the compositions of the invention for modulating the activity of RNA comprise heterocyclic structures having at least one RNA cleaving moiety or some other moiety capable of interacting with an RNA appended thereto. Certain of these compositions are adapted for delivery of the RNA cleaving (i.e., intercalating or minor-groove-binding) moiety to a predetermined portion of the RNA strand, in part by carefully selecting the sites for attachment of the heterocyclic RNA cleaving moieties to the antisense oligonucleotide or analog. Compositions of the invention may include naturally occurring or non-naturally occurring sugar portions, as well as naturally occurring or non-naturally occurring base portions. Accordingly, novel nucleosides and nucleoside analogs are provided. Such nucleosides and nucleoside analogs may be incorporated into oligonucleotides which are useful in the practice of the invention.

The invention also is directed to methods for modulating the activity of an RNA comprising contacting an organism having the RNA with a composition formulated in accordance with the foregoing considerations. It is preferred that the RNA which is to be modulated be preselected to comprise preferably messenger RNA which codes for a protein whose formation is to be modulated. The invention may also be applied to pre-messenger RNA and, indeed, to RNA generically and to single-stranded DNA. The targeting portion of the composition to be employed is selected to be complementary to the preselected portion of RNA or single stranded DNA, that is, to be an antisense oligonucleotide for that portion.

This invention is also directed to methods for treating an organism having a disease characterized by the undesired production or overproduction of a protein, comprising contacting the organism with a composition in accordance with the foregoing considerations, preferably a composition which is designed to specifically bind with messenger RNA which codes for the protein whose production is to be modulated or inhibited.

The invention is also directed to the utilization of groups in addition to the reactive functional groups that are further appended to oligonucleotides. Such pendant groups may lead to enhanced oligonucleotide uptake, enhanced resistance of oligonucleotide to degradation by nucleases, and stronger binding of the oligonucleotides to targeted RNA. Further functionalities may serve to attach reporter groups such as biotin and various fluorophores to sequence-specific oligonucleotides for diagnostic purposes. More than one non-reactive functionality may be attached to each oligonucleotide, two or more non-reactive functionalities may be attached to a single nucleoside unit, and a combination of non-reactive functionalities and reactive functionalities may be attached to a single nucleoside unit or a single oligonucleotide.

Nuclease resistant oligonucleotides of this invention consist of a single strand of nucleic acid bases linked together through linking groups. The target portion of the nuclease resistant oligonucleotide may range in length from about 5 to about 50 nucleic acid bases. However, in accordance with the preferred embodiment of this invention, a target sequence of about 15 bases in length is believed to be optimal.

The bases of the individual nucleotides comprising the oligonucleotides of the invention may be pyrimidines such as thymine, uracil or cytosine, or purines such as guanine or adenine, or both, arranged in a specific sequence. Additionally, they may be any of the synthetic bases known in the art. The sugar moiety the nucleotides may be of the deoxyribose or ribose type or may be a synthetic sugar known in the art. The phosphate linking groups of the oligonucleotides of the invention may be native or wild type phosphodiester linkages or synthetic linking groups such as, for example, phosphorothioate, phosphorodithioate, methylphosphonate, or alkylphosphonate. For nuclease resistance synthetic linkages are preferred.

The resulting novel oligonucleotides are resistant to nuclease degradation and exhibit hybridization properties of higher quality relative to wild type (DNA-DNA and RNA-DNA) duplexes and the phosphorus modified oligonucleotide antisense duplexes containing phosphorothioates, methylphosphonates, phophoramidates and phosphorotriesters.

The invention further is directed to diagnostic methods for detecting the presence or absence of abnormal RNA molecules or abnormal or inappropriate expression of normal RNA molecules in organisms or cells. It is also directed to methods for the selective cleaving of RNA useful in research and diagnostics. Such selective cleaving is accomplished by interacting RNA with compositions of the invention which have reactive portions capable of effecting such cleavage and targeting portions designed to enforce selectivity.

The invention is also directed to methods for modulating the production of a protein by an organism comprising contacting the organism with a composition formulated in accordance with the foregoing considerations. It is preferred that the RNA or DNA portion which is to be modulated be preselected to comprise that portion of DNA or RNA which codes for the protein whose formation is to be modulated. The targeting portion of the composition to be employed is, thus, selected to be complementary to the preselected portion of DNA or RNA, that is, to be an antisense oligonucleotide for that portion.

This invention is also directed to methods of treating an organism having a disease characterized by the undesired production of a protein. This method comprises contacting the organism with a composition in accordance with the foregoing considerations. The composition is preferably one which is designed to specifically bind with messenger RNA which codes for the protein whose production is to be inhibited.

The invention further is directed to diagnostic methods for detecting the presence or absence of abnormal RNA molecules or abnormal or inappropriate expression of normal RNA molecules in organisms or cells.

The invention is also directed to methods for the selective binding of RNA for research and diagnostic purposes. Such selective, strong binding is accomplished by interacting such RNA or DNA with compositions of the invention which are resistant to degradative nucleases and may hybridize more strongly and with greater fidelity than any other known oligonucleotide.

In accordance with a further embodiment of the invention, novel processes are provided for the synthesis of novel nucleoside analogs that are substituted in the 2' position and which are useful for incorporation into oligonucleotides of the invention. Such process provides for introduction of a 2' substituent in the absence of blocking of either the 3' or 5' hydroxyl groups of a ribofuranosyl nucleoside. For adenosine and cytidine, such processes utilize treatment with sodium hydride followed by use of an alkyl halide. For uridine, such processes utilize treatment with stannous chloride and an alkyl halide. For guanosine, such processes treat 2,6-diamino purine riboside with sodium hydride and alkyl halide followed by deamination to the guanosine compound as is disclosed in U.S. patent application Ser. No. 918,362, filed Jul. 23, 1992, the entire disclosure of which is herein incorporated by reference. The reactions are conducted at or near room temperature. These conditions are contrasted to prior known processes that require strong alkylating agents, for instance diazomethane. Such strong alkylating agents necessitate the complete protection of all reactive sites on the nucleoside bases and the 3' and 5' sugar hydroxyls.

Certain compositions useful for modulating the activity of an RNA or DNA molecule in accordance with this invention generally comprise a sugar modified oligonucleotide containing a targeting sequence which is specifically hybridizable with a preselected nucleotide sequence of single stranded or double stranded DNA or RNA molecule and which is nuclease resistant.

It is generally desirable to select a sequence of DNA or RNA which is involved in the production of proteins whose synthesis is ultimately to be modulated or inhibited in entirety. The oligonucleotide sequence is synthesized, typically through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length which may be desired.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

Figure 1A:
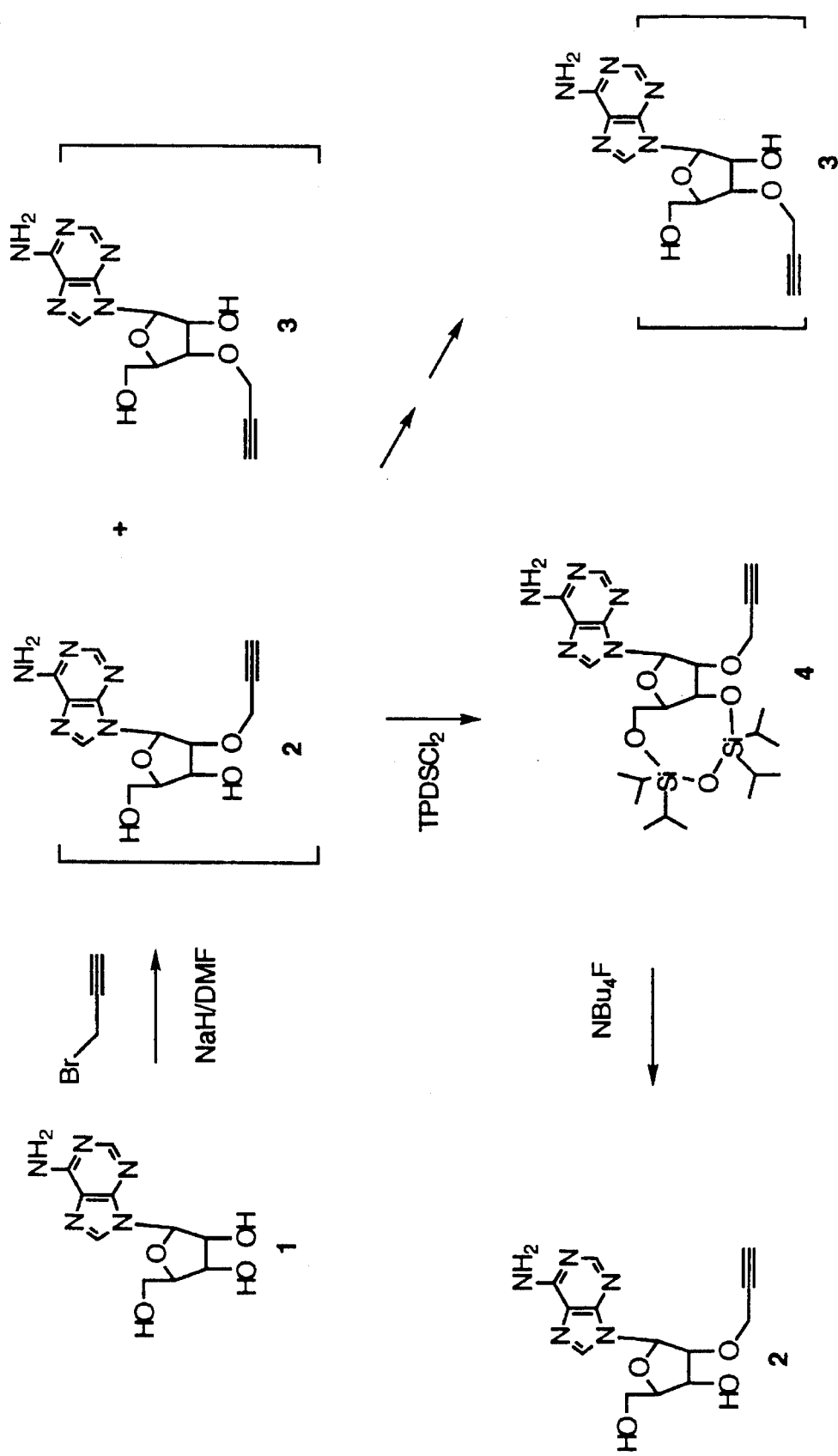
FIG. 1 provides a general synthetic scheme for compound 14.

In the context of this invention, the term "oligonucleotide" refers to polynucleotides formed from a plurality of nucleotide units that contain naturally-occurring bases and pentofuranosyl sugars and that are that are joined by phosphodiester linkages. The term "oligonucleotide" thus includes naturally occurring species or synthetic species formed from naturally occurring nucleotide units.

The term "oligonucleotide" also includes polynucleotides formed from non-naturally occurring or modified subunits. These modifications can occur on the base portion of a nucleotide, on the sugar portion of a nucleotide or on the linkage joining one nucleotide to the next. In addition, modification can be made wherein nucleoside units are joined through groups that substitute for the internucleoside phosphate or sugar phosphate linkages. Such linkages include the those disclosed in U.S. patent applications Ser. No. 566,836, filed Aug. 13, 1990, entitled Novel Nucleoside Analogs, issued as U.S. Pat. No. 5,223,618; Ser. No. 703, 619, filed May 21, 1991, entitled Backbone Modified Oligonucleotide Analogs, issued as U.S. Pat. No. 5,378,825; Ser. No. 903,160, filed Jun. 24, 1992, entitled Heteroatomic Oligonucleoside Linkages, abandoned; Ser. No. PCT/US92/04294, filed May 21, 1992, entitled Backbone Modified Oligonucleotides; and Ser. No. PCT/US92/04305, all assigned to the assignee of this invention. Other modifications can be made to the sugar, to the base, or to the phosphate group of the nucleotide. Exemplary modifications are disclosed in U.S. patent applications: Ser. No. 463,358, filed Jan. 11, 1990, entitled Compositions And Methods For Detecting And Modulating RNA Activity, abandoned; Ser. No. 566,977, filed Aug. 13, 1990, entitled Sugar Modified Oligonucleotides That Detect And Modulate Gene Expression, abandoned; Ser. No. 558,663, filed Jul. 27, 1990, entitled Novel Polyamine Conjugated Oligonucleotides, issued as U.S. Pat. No. 5,138,045; Ser. No. 558,806, filed Jul. 27, 1991, entitled Nuclease Resistant Pyrimidine Modified Oligonucleotides That Detect And Modulate Gene Expression, abandoned; and Ser. No. PCT/US91/00243, filed Jan. 11, 1991, entitled Compositions and Methods For Detecting And Modulating RNA Activity; Ser. No. 777,670, filed Oct. 15, 1991, entitled Oligonucleotides Having Chiral Phosphorus Linkages, issued as U.S. Pat. No. 5,212,295; Ser. No. 814,961, filed Dec. 24, 1991, entitled Gapped 2' Modified Phosphorothioate Oligonucleotides, abandoned; Ser. No. 808,201, filed Dec. 13, 1991, entitled Cyclobutyl Oligonucleotide Analogs, issued as U.S. Pat. No. 5,359,044; and Ser. No. 782,374, filed Oct. 24, 1991, entitled Derivatized Oligonucleotides Having Improved Uptake & Other Properties, abandoned, all assigned to the assignee of this invention. The disclosures of all of the above noted patent applications are incorporated herein by reference.

Thus, the term oligonucleotide can refer to structures that include modified portions (e.g., modified sugar moieties, modified base moieties or modified sugar linking moieties) that function in a manner similar to natural bases, natural sugars and natural phosphodiester linkages. Representative modifications include phosphorothioate, phosphorodithioate, methyl phosphonate, phosphotriester or phosphoramidate inter-nucleoside linkages in place of phosphodiester inter-nucleoside linkages; deaza or aza purines and pyrimidines in place of natural purine and pyrimidine bases; pyrimidine bases having substituent groups at the 5 or 6 position; purine bases having altered or replacement substituent groups at the 2, 6 or 8 positions; sugars having substituent groups at, for example, their 2' position; or carbocyclic or acyclic sugar analogs. Other modifications consistent with the spirit of this invention are known to those skilled in the art. Such oligonucleotides are best described as being functionally interchangeable with, yet structurally different from, natural oligonucleotides (or synthetic oligonucleotides along natural lines). All such oligonucleotides are comprehended by this invention so long as they can effectively mimic the structure of a desired RNA or DNA strand.

The targeting portions of the compositions of the invention preferably are oligonucleotides having from about 3 to about 50 base units. It is preferred that such oligonucleotides have from about 8 to about 40 base units, more preferably from about 12 to about 25 base units, even more preferably about 15 base units. The targeting portion should be adapted to be specifically hybridizable with the preselected nucleotide sequence of the RNA selected for modulation.

The oligonucleotides believed to be suitable for the practice of the invention comprise one or more subunits having general structure (1a)

wherein Bx is any of the purine or pyrimidine bases, including those which are known for naturally occurring and non-naturally occurring oligonucleotides or which exhibit similar functions; (E) is attached at one or more of the indicated positions and is an RNA cleaving moiety, a group for improving the pharmacokinetic properties of said oligonucleotide, a group for improving the pharmacodynamics of said oligonucleotide, H, OH, or other substituent groups; $S_g$ is a naturally-occurring or non-naturally occurring sugar; and L is a sugar-linking group. The sugar-linking group L may be any of those structures either naturally occurring, described herein, or otherwise known which are capable of linking sugar moieties of oligonucleotides or sugar analogs to form the targeting portion of the compositions of this invention. It is preferred that these sugar-linking functions comprise either a phosphodiester structure; a phosphodiester structure wherein at least some of the phosphodiester bonds of said oligonucleotide are substituted with phosphorothioate, methyl phosphonate, or alkyl phosphate; or a structure described in one of the patent applications incorporated by reference.

Persons skilled in the art will recognize that variations in the structures of the sugar moieties of the subject compositions can be made without deviating from the spirit of the invention. It is not necessary that every sugar-linking function be in a modified form. A substantial number and even a predominance of such linking groups can exist in the native, phosphodiester form as long as the overall targeting portion of the composition exhibits an effective ability to specifically bind with a target to form a hybrid capable of detecting and modulating the RNA activity. Of course, fully unmodified, native phosphodiester structures can be used as well.

It is not necessary to tether more than one or perhaps two RNA cleaving functionalities in order to provide the benefits of the invention. Thus, an RNA cleaving moiety preferably is tethered to a relatively small proportion of the subunits, generally only one or two, that together comprise the oligonucleotide that is the targeting portion of a composition of the invention. In other embodiments, however, all of the nucleotides in an oligonucleotide can be modified to include one or more RNA cleaving moieties. In even further embodiments, one or more or even all of the nucleotides (including those that also carry an RNA cleaving functionality) include pharmacodynamic improving groups or pharmacokinetic improving groups tethered thereto.

It is believed desirable in accordance with certain preferred embodiments to attach the RNA cleaving portion and the intercalating portion of the compositions of this invention to one of the nucleosides forming a subunit of the targeting portion. Such an attachment is depicted by expanding structure (1a) to structure (1b):

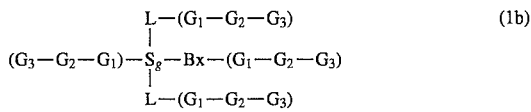

wherein $G_1$ is a bivalent linker, $G_2$ is an aryl or heteroaryl or aryl or heteroaryl containing group and $G_3$ is an RNA cleaving moiety having general acid/base properties. In even further preferred embodiments of the inventions, $G_3$ further includes an electrophilic catalyst.

Bivalent linker $G_1$ preferably contains both a heteroatom ($G_{1'}$) and an alkyl, alkenyl or alkynyl group ($G_{1''}$) directly in the atomic backbone that leads from the $S_g$, Bx or L group to the $G_2$ group. Preferred heteroatoms include O, S, and N-H or N-alkyl. It is also preferred that $G_1$ connects to a 2' sugar position of internucleoside linkage thereof.

$G_2$ preferably is a polycyclic moiety having from 2 to 6 rings, at least 2 of said rings being joined to form an electronically conjugated system. Representative $G_2$ groups include naphthalene, anthracene, phenanthrene, benzonaphthalene, fluorene, carbazole, acridine, pyrene, anthraquinone, quinoline, phenylquinoline, xanthene or 2,7-diazaanthracene groups. Structures of this type preferably act as intercalators. Other intercalators believed to be useful are described by Denny, *Anti-Cancer Drug Design* 1989, 4, 241.

RNA-cleaving group $G_3$ can be a functionality that has both general acid and general base characteristics. It also can possess electrophilic catalytic characteristics. While we do not wish to be bound by any particular theory, general acid/base moieties are believed to function by first deprotonating a target (the general base function). The deprotonated target then can attack a phosphodiester linkage between adjacent nucleotides. The general acid properties are manifested by protonation of an oxygen atom within the phosphodiester linkage. A 2'-hydroxyl group typically is the target of the general base such that a 2'-oxygen-centered anion serves as a nucleophile towards the phosphodiester linkage. The 5'-hydroxyl or the phosphate oxygen is protonated by the general acid and serves as a leaving group. The overall result is cleavage of a phosphodiester linkage between a phosphate group and a 5' hydroxyl group. This process can be further assisted by the provision of an appropriate electrophilic catalytic group or groups in close proximately to the phosphate. Such electrophilic catalytic groups are described by H. Dugas, *Bioorganic Chemistry, A*

*Chemical Approach to Enzyme Action*, 2nd Ed., Springer-Verlag, N.Y., 1989.

The above-described general acid/base mechanism and the general acid/base mechanism augmented with electrophilic catalysis thus excludes the nitrogen mustards (see, e.g., Kohn, et al., *Nucleic Acid Research* 1987, 24, 10531 for a review of nitrogen mustard type molecules), photoactive molecules such as psoralens (see, e.g., Cimino, et al., *Ann Rev. Biochem.* 1985, 54, 1151 for a review of photoactive psoralens), and the alkylating agents described by Vlassov, et al., *Nucleic Acids Research* 1986, 14, 4065.

In preferred embodiments, $G_3$ includes a 5- or 6-membered heterocyclic ring, preferably a heterocyclic ring that contains at least one nitrogen atom, more preferably at least one imidazole group. A more preferred group for $G_3$ includes an imidazole, a C2-substituted imidazole, an imidazole substituted at one of its C4 or C5 positions with an electrophilic catalyst, a bis-imidazole, a C2-substituted bis-imidazole, a bis-imidazole wherein at least one C4 or C5 position is substituted with an electrophilic catalyst, a bisimidazole wherein both of its C4 positions or both of its C5 positions are substituted with electrophilic catalyst or a bis-imidazole wherein the linkage connecting the individual imidazole rings of the bis-imidazole is substituted with an electrophilic catalyst. The electrophilic catalyst preferably includes a nitrogen functionality that can be protonated, preferably an amine, a nitrogen heterocycle, guanidine or amidine. In preferred embodiments of the invention, these nitrogen functionalities are "preorganized" for optimal interactions with one or more of the three oxygen atoms of a phosphate backbone of a target nucleic acid.

Bis-imidazoles are also preferred general acid/base RNA cleavers. Bis-imidazole moieties are those wherein two imidazole rings are joined via a linking group. Bis-imidazoles can be prepared utilizing the general procedures described by Tang, et al., *J. Am. Chem. Soc.* 1978, 100, 3918. The linking groups connecting bis-imidazoles will include one or more tethering groups for connecting the bis-imidazole to other functionality. Preferred tethering groups are hydroxyl, carboxy, amine and thiol groups; hydroxyl and carboxy groups are particularly preferred. Other tethering groups include planar aromatic ring systems. The carboxy moiety allows for tethering the bis-imidazole via ester and amide linkages.

$G_2$ and $G_3$ can be connected by a single covalent bond or by a mono- or polyatomic bivalent linker. Covalent bonds and bivalent linkers also can be used in tandem to connect between the $G_2$ and $G_3$ groups through, for example, two different atomic positions on each group. The bivalent linker can include an electrophilic catalyst directly in the atomic backbone leading from $G_2$ to $G_3$ or attached to the backbone in a pendant fashion. In preferred embodiments, $G_3$ includes at least one imidazole group and a single covalent bond and/or bivalent linker at position C4 and/or C5 of such imidazole group leading to the $G_2$ group. With use of both a single covalent bond and a bivalent linker, two tandem points of connections are provided between the $G_3$ and the $G_2$ groups.

In other preferred embodiments, $G_3$ includes two imidazole rings linked to $G_2$ via one or more one of an acyl, an amine, a thiol, an aryl, a substituted aryl, an alkyl or a substituted alkyl or combinations of these groups. As used herein acyl groups include keto, carboxyl, ester and amide linkages and combinations of amines and thiol includes sulfamides. Amides are particularly preferred since they are stable to the reactions conditions normally utilized during oligonucleotide synthesis utilizing commercial DNA synthesizers and commercial reagents.

Certain preferred compounds according to the invention have structure (1c):

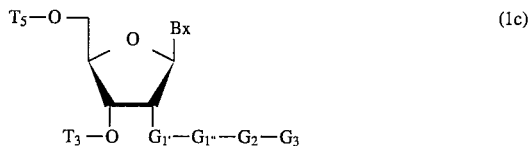

(1c)

wherein G1', $G_{1''}$, $G_2$ and $G_3$ are as defined above and $T_5$ is H, a hydroxyl protecting group, a phosphate group, a nucleotide or an oligonucleotide; $T_3$ is H, a hydroxyl protecting group, a nucleotide, an oligonucleotide, a phosphate group, an activated phosphate group or a solid phase support; and Bx is a heterocyclic base moiety, preferably a purine. In certain useful synthetic intermediates of the invention, $G_1$-$G_2$-$G_3$ is alkynyl, preferably propargyl, provided that when Bx is uracil then $T_3$ and $T_5$ are not H or acetyl. 2'-O-propargyl moieties have been used as intermediates in the synthesis of certain caged borane compounds or as structural analogs to AZT (see, Anisuzzaman, et al., *Polyhedron* 1990, 9, 891; Solway, *Pure & appl. Chem.* 1991, 63, 411; and Rosowsky, et al., *Nucleosides & Nucleotides* 1989, 8, 491). As shown in the examples below, the propargyl linkage can be stepwise reduced to a propene and then a propyl linkage. The propargyl, propene or propyl nucleoside intermediates are potentially useful as antiviral agents.

Compounds having structure (1c) wherein $T_5$ and $T_3$ are hydroxyl protecting groups and GI,, is alkynyl preferably are prepared by contacting a compound having structure (1d) with a compound having structure $T_6O$-$G_2$-$OT_6$ in the presence of a nucleophile and a palladium catalyst to produce a compound having structure (1e). In this structure $T_6$ is a hydroxyl activating group such as trifluoromethylsulfonyl (a triflate or trf group).

(1d)

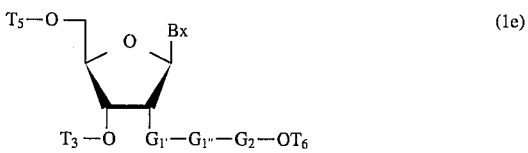

(1e)

In treating compound (1d) to form compound (1e) use of the $T_3$ and $T_5$ hydroxyl blocking groups is optional. Use of such blocking groups allows for the initial preparation of the compound (1d) under more rigorous reaction conditions since concurrent substitution of either the 3' or 5' hydroxyl group during substitution of the 2'-hydroxyl group need not be considered. If blocking groups are not utilized, in preparing compound (1d), 2'-O substitution is conducted in a regioselective manner to selectively substitute (or predominantly selectively substitute) the 2' position in preference to the 3' or 5' positions. If $T_3$ and/or $T_5$ blocking groups are selected, since essentially pH neutral reaction conditions are utilized in converting compound (1d) to compound (1e), consideration of acid or base stability of the $T_3$ and $T_5$ hydroxyl blocking groups is not necessary. Thus, various of the known hydroxyl blocking groups can be utilized. Such blocking groups can be selected from those known to the art skilled. A recent review of such blocking groups is found in Beaucage, et al., *Tetrahedron* 1992, 48, 2223. A particularly useful blocking groups is the tetraisoproyldisiloxanyl group since it concurrently blocks both the 3' and the 5' hydroxyl positions. Thus in preferred embodiments, T₃ and T₅ together form a 3',5 '-O-tetraisoproyldisiloxanyl group.

T₆ is selected such that T6O is a good leaving group. Preferably, T₆ is trifluoromethylsulfonyl. Other suitable leaving groups include iodo and bromo. Displacement of the T₆ leaving group is conducted in the presence of a catalyst, preferably a palladium catalyst. One preferred palladium catalyst is Pd(PPh₃)₄. A further palladium catalyst in PdCl₂(PPh₃)₂.

Compound (1e) then is contacted with a compound having structure T₇-G₃-M-T₈ to form compound (1c). This reaction also is effected in the presence of a catalyst. As with the above-described catalytic reaction, palladium (preferably Pd(PPh₃)₄) is selected as the catalyst. In palladium-catalyzed reactions M preferably is selected to be Sn. T₈ should be a poly-alkyl group with alkyl being from about 1 to about 5 carbon atoms. Preferably T₈ is tris-butyl. T₇ is a regio protecting group or is R_C as outlined below. Such R_C groups also can include appropriate protecting groups. Presently preferred regio protecting groups include a t-butyldimethylsilyl or t-butyldimethylsilyl group.

A number of particularly preferred compounds of the invention have structures (2a)–(5c):

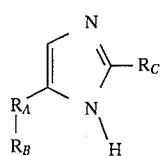  (2a)

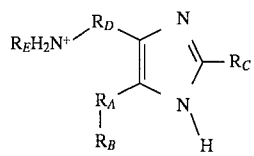  (2b)

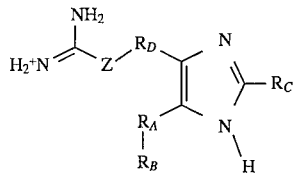  (2c)

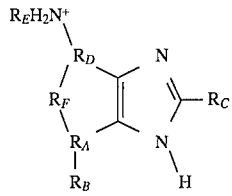  (3a)

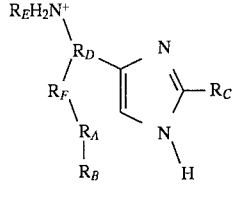  (3b)

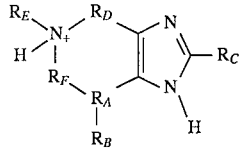  (4a)

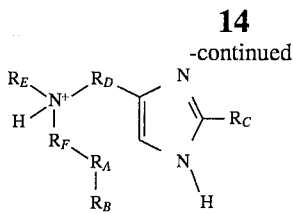  (4b)

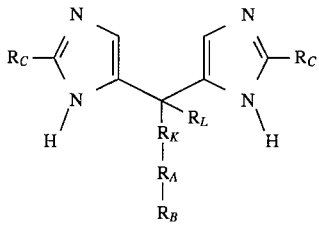  (5a)

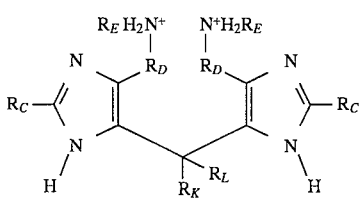  (5b)

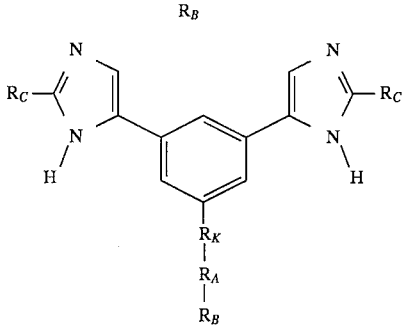  (5c)

wherein:

R_A is aryl, substituted aryl, or nitrogen heterocyclic;

R_B is $S_g$-$G_1$·$G_{1''}$-, $S_g$-, Bx-, or L-;

R_C is H, O⁻, COO⁻, OR_G, NH₂, C(R_G)(R_H)(R_J), N(R_G)(R_H)(R_J), Cl, Br, F, CF₃, SR_G, NHC(O)R_G, OC(O)R_G, NO, nitrogen heterocyclic or another electron donating group;

R_D is CH or (CH₂)_q;

R_E is H, (CH₂)_n-R_J, or a chemical functional group comprising R_J;

R_F is C₁-C₂₀ alkyl, C₂-C₂₀ alkenyl or C₂-C₂₀ alkynyl, aryl, or cycloalkyl;

R_G, R_H, and R_J are, independently, H, C₁-C₁₀ alkyl, or substituted alkyl;

R_J is H, nitrogen heterocyclic, a positively charged group, or a phosphoryl hydrogen bond donating group;

R_K is alkyl, acyl or acyl-alkyl;

R_L is H or OH;

Z is NH₂ or CH₂;

Bx is a purine or pyrimidine base or a derivative thereof;

L is a sugar-linking group;

$S_g$ is a naturally occurring or non-naturally occurring sugar;

$G_{1'}$ is O, S, NH or N-alkyl;

$G_{1''}$ is C₁-C₂₀ alkyl, C₂-C₂₀ alkenyl or C₂-C₂₀ alkynyl;

n is from about 1 to about 5; and q is from about 0 to about 5.

$R_A$ preferably is selected to promote intercalation between the base pairs of the oligonucleotide/RNA target sequence heteroduplex. $R_A$ is selected such that it will make a major contributions to the net intercalative binding energy. The other contributions to the net intercalation energy is derived from the imidazole ring portion of structures (2a)–(5c). Representative $R_A$ include phenyl, substituted phenyl, naphthyl, anthracenyl, 2,7-diaza-anthracenyl, pyrenyl, acridinyl, 9-aminoacridinyl, quinolinyl and pyridinyl moieties. $R_A$ preferably is a polycyclic aromatic hydrocarbon such as a naphthyl residue. Preferred polycyclic aromatic hydrocarbons are non-carcinogenic moieties that do not bind RNA or DNA with either high affinity or a strong sequence dependence.

According to the present invention, $R_B$ is a covalent linker joining $R_A$ to a sugar moiety, to a base moiety, or to an alkyl or alkoxy sugar-linking moiety. In certain preferred embodiments, $R_B$ is $S_g$-2'-O-$CH_2$-$CH_2$- or $S_g$-2'-O-$(CH_2)_3$-NH-CO-.

$R_C$ preferably is electron donating, through inductive and/or resonance effects. It is believed that $R_C$ serves to upwardly adjust the $pK_a$ of the imidazole residue in structures (2a)–(5c). In a steric sense, $R_C$ is intended to lie in the RNA minor groove without affecting RNA hybridization or intercalative binding via $R_A$ and/or the imidazole residue. $R_C$ may be designed to contain a proton-accepting group to assist deprotonation of the 2' hydroxyl of a target RNA.

$R_D$ preferably is a covalent linker joining the 5-position of the imidazole residue and the amine function, $H_2R_EN^+$. $R_D$ preferably comprises about 1–5 carbon atoms. However, $R_D$-$N^+H_2R_E$ need not be present. As will be recognized, the existence of the amine function in either protonated or neutral form is media dependent. The amine function is intended to lie in one of the RNA major or minor grooves and to complex with the RNA internucleotide phosphate diester through electrostatic and/or hydrogen bonding to RNA phosphate oxygens. Such complexation is intended to properly orient RNA cleaving moieties such as the imidazole residue and to directly enhance the rate of cleavage. Such rate enhancement is believed to be effected through polarization and weakening of RNA phosphorus-oxygen bonds, making the phosphorus atom more electrophilic and more reactive to attack by a 2'-oxygen atom. The amine function is also believed to stabilize the resulting transition states and intermediates, making the phosphate oxygens better proton acceptors.

In preferred embodiments, $R_E$ comprises an alkyl chain of up to about 3 carbon atoms and a further moiety known to assist RNA cleaving, $R_J$. Preferably, $R_J$ is a nitrogen heterocycle, more preferably an imidazole. This function is intended to pre-protonate one of the two non-ester linkage phosphoryl oxygens in an initial chemical step to make the phosphorus more electrophilic and reactive to attack by a 2' oxygen anion, $O^-$. It is particularly preferred that $R_J$ have one of the structures:

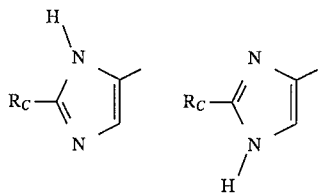

where $R_C$ is as defined above or is a group that can hydrogen bond with or electrostatically interact with phosphate oxygens. In other preferred embodiments, $R_J$ is guanidino or amidino. Such structures are selected for further electrophilic complexation of the phosphate backbone of a target nucleic acid. Guanidine and amidine structures are illustrated in structure (5c).

$R_F$ is a conformation-restricting moiety of variable size linking $R_A$ and the amine function. It can be mono- or polycyclic and/or acyclic, as well as saturated and/or unsaturated. $R_F$ preferably is $(CH_2)_n$ where n is 1–3.

Three representative imidazole-based, RNA-cleaving oligonucleotides according to the present invention are depicted by structures (11)-(13), wherein DMT is dimethoxytrityl, CEO is cyanoethoxy, and Bz is benzoyl. The latter are protective blocking groups of synthesis.

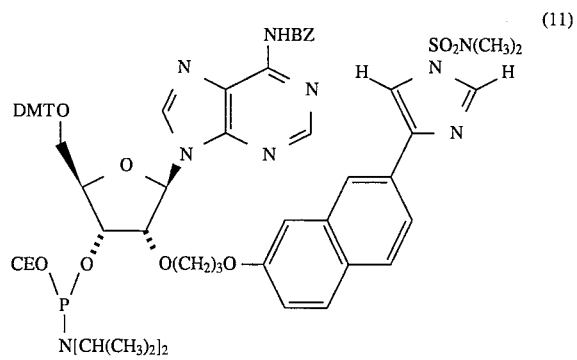

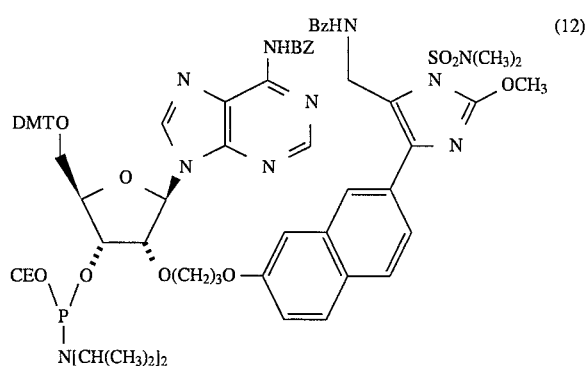

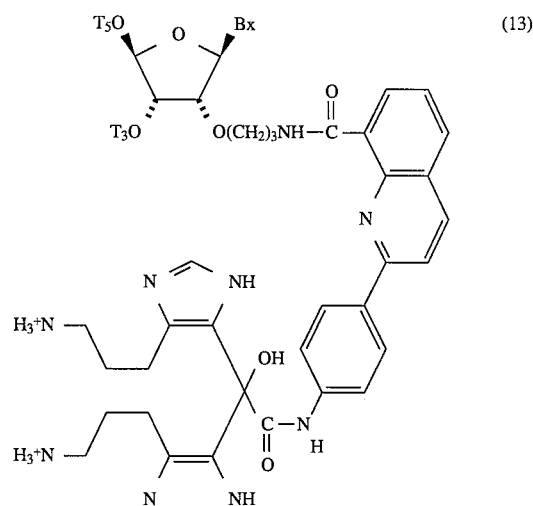

While not intending to be limited to any particular theory of the invention, it is believed that when the oligonucleotides of the present invention hybridize with RNA, the $R_A$ and, to a lesser extent, any imidazole subunits appended to the 2' positions thereof, intercalate with the RNA and thereby are constrained by the hybrid duplex to a fairly limited number of positions and conformations in comparison to designs lacking the intercalative moiety. By constraining the intercalative cleaver with the duplex in this manner, the specific RNA cleaving functionality is positioned for optimal delivery to hybridized RNA. It should be noted that limited local motion and positioning via the intercalative mode are allowed, such that the positively charged amine of structures (2b)–(5c) can optimally fine-tune the orientation of the entire composition by hydrogen bonding and electrostatic interactions with the phosphate groups while retaining an intercalative binding mode. Accordingly, it is intended that the present invention include as a preferred embodiment all compositions comprising a ribofuranosyl nucleotide which bears at its 2' position substituents capable of both intercalating and cleaving RNA. The same substituents capable of both intercalating and cleaving RNA also may be functionalized via a suitable linker to any of the bases or to the oligonucleotide backbone.

It will be recognized that structures (2a)–(5c) can be coupled with the sugar portion of a given nucleoside at a variety of positions including, but not limited to, the 2' hydroxyl group as shown, for example, in structures (14) and (15):

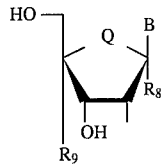
(14)

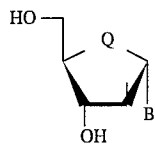
(15)

wherein:

Q is O or $CR_{11}$;

$R_8$ and $R_9$ are H, lower alkyl, substituted lower alkyl, a group which improves the pharmacokinetic properties of an oligonucleotide, a group which improves the pharmacodynamic properties of an oligonucleotide, or one of structures (2a)–(5c), absent the $R_B$ group;

$R_{11}$ is H, lower alkyl, substituted lower alkyl, an RNA cleaving moiety, a group which improves the pharmacokinetic properties of an oligonucleotide, or a group which improves the pharmacodynamic properties of an oligonucleotide; and Bx is a nucleoside base or blocked nucleoside base moiety.

Alkyl groups of the invention include but are not limited to $C_1$–$C_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methyl-pentyl, 3-methylpentyl, 2-ethylhexyl and 2-propylpentyl. Alkenyl groups include but are not limited to unsaturated moieties derived from the above alkyl groups including but not limited to vinyl, allyl and crotyl. Alkynyl groups include unsaturated moieties having at least one triple bond that are derived from the above alkyl groups including but are not limited to ethynyl and propargyl. Aryl groups include but are not limited to phenyl, tolyl, benzyl, naphthyl, anthracyl, phenanthryl, pyrenyl, and xylyl. Halogens include fluorine, chlorine and bromine. Suitable heterocyclic groups include but are not limited to imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Amines are also meant to include polyalkylamino compounds and aminoalkylamines such as aminopropylamine and further heterocyclo-alkylamines such as imidazol-1, 2 or 4-yl-propylamine. Substituent groups for the above include but are not limited to other alkyl, haloalkyl, alkenyl, alkoxy, thioalkoxy, haloalkoxy and aryl groups as well as halogen, hydroxyl, amino, azido, carboxy, cyano, nitro, mercapto, sulfides, sulfones and sulfoxides. Other suitable substituent groups also include rhodamines, coumarins, acridones, pyrenes, stilbenes, oxazolo-pyridocarbazoles, anthraquinones, phenanthridines, phenazines, azidobenzenes, psoralens, porphyrins and cholesterols.

The nucleosidic sites to which functionality may be attached, and the design of any intervening linker group, are critical to the design of compositions for sequencespecific destruction or modulation of targeted RNA. The functionality must not interfere with Watson-Crick base pair hydrogen bonding rules, as this is the sequence-specific recognition/binding factor essential for selection of the RNA to be disrupted. The nucleosidic sites of functionalization also must not preclude optimal placement of the functionalized composition to best fulfill structural and functional goals.

Approaches to perfect complementation between the modified oligonucleotides and targeted RNA will result in the most stable heteroduplexes. This is desired because the heteroduplex must have a half-life sufficient to allow the reactive or non-reactive functionalities of this invention to initiate RNA cleavage or disruption of RNA function.

The half life of a perfectly formed duplex will be greatly affected by the positioning of the tethered functional group. Inappropriate positioning of functional groups, such as placement on the Watson/Crick base pair sites, would preclude duplex formation. Other attachment sites may allow sequence-specific binding but may be of such low stability that the reactive functionality will not have sufficient time to initiate RNA disruption.

For RNA inactivation, another important factor concerning the placement of the tethered functionality is that it must have optimized molecular recognition with the receptive substrate located in the targeted RNA, for example of a general base group with the 2'-hydroxyl group. A variety of structural studies such as X-ray diffraction, chemical reaction, and molecular modeling may aid in this placement.

Those positions on the nucleosides of double-stranded nucleic acids that are exposed in the minor groove may be substituted without affecting Watson-Crick base-pairing or duplex stability. Such sites are preferred for attachment of the reactive functionalities of the invention. The reactive functionalities attached to these positions in accordance with this invention may initiate cleavage and destruction of targeted RNA or interfere with its activity.

Reactive functionalities or pendant groups of oligonucleotides previously described in the literature have been almost exclusively placed on a phosphorus atom, the 5position of thymine, or the 7-position of purines. A phosphorus atom attachment site can allow a reactive group to access both the major and minor grooves or to intercalate between base pairs. However, internal phosphorus modification can result in greatly reduced heteroduplex stability except with intercalator placement. Attachments at the 3' and/or 5' ends are limiting in that only one or two functional groups can be accommodated in the oligonucleotide. Even successful cleavage will not drive turnover. Functionality placed in the 5-position or 7-position of heterocycles (bases) pyrimidine and purine respectively will reside in the major groove of the duplex and will not be in proximity to the RNA 2'-hydroxyl substrate. However, such functional placement may be used to link to an intercalator bound between base pairs. Further, such placement can interfere with Watson-Crick binding.

Pendant groups that do not cleave RNA also can be attached to the oligonucleotides of the invention. In certain embodiments, such groups do not possess a reactive functionality but serve to enhance the pharmacodynamic and/or pharmacokinetic properties of an oligonucleotides. In this context, pharmacodynamic property improvement means improved oligonucleotide uptake, enhanced oligonucleotide resistance to degradation, and/or strengthened sequence-specific hybridization with RNA. Pharmacokinetic property improvement means, in this context, improved oligonucleotide uptake, distribution, metabolism or excretion. Such pendant groups do not initiate chemical reactions. They preferably include alkyl chains, polyamines, ethylene glycols, polyamides, aminoalkyl chains, amphipathic moieties, points for reporter group attachment, and intercalators attached to any of the preferred sites for attachment.

It is possible that other positions will be found for attachment of the RNA cleaving moieties to nucleosides, nucleotides, or oligonucleotides, particularly when further modification of the purine or pyrimidine structure is undertaken or when backbone analogs suitable for functionalization are found, as may be done by persons of ordinary skill in the art without deviating from the spirit of the present invention. It will be understood that preferably one or at most a few RNA cleaving moieties generally should be employed. Thus, artisans in the field will have great latitude in selecting means of attachment of the RNA cleaving moieties, the pharmacodynamic improving groups or the pharmacokinetic improving groups in accordance with this invention.

The RNA cleaving moieties of the compositions of the present invention are designed in such a fashion that they can be effective in performing their proximate task, leading to the desired modulation of RNA activity. It is believed to be useful to employ heteroatomic substitutions in the RNA cleaving moieties of these molecules, especially amides and polyamides, and indeed some may be preferred in order to ensure even tighter binding between the target mRNA and the compositions of the invention.

The nucleosides of the invention are linked together and to the rest of the oligonucleotide through a sugar-linking group. The linking group may be any of those structures described herein that are capable of linking sugar moieties of oligonucleotides together to form the targeting portion of the compositions of this invention. It is preferred that these sugar-linking groups comprise the phosphodiester structure or a derivative thereof. Derivatives of the phosphodiester structure may include substitution of a sulphur, methyl, methyl oxide, or amine group for an oxygen. The sugar phosphate nucleic acid backbone may be modified as a phosphorothioate, phosphorodithioate, methylphosphonate, or phosphate alkylated moiety. The phosphodiester linkage may also be replaced by a carbon or ether linkage as discussed above.

Without desiring to be bound by any particular theory of operation, it is believed that the reactive RNA cleaving functionalities described in this invention work by mechanisms involving any or all of:
1. phosphodiester bond cleavage via general acid/base catalysis with or without assistance via H-bonding, electrostatic interactions, or electrophilic catalysis;
2. backbone sugar cleavage;
3. base alkylation cleavage; or
4. sugar alkylation, i.e., 2'-hydroxyl cross-linking.

One important aspect of this invention is the position and orientation of an appropriate reactive functionality of the targeting portion of this invention and the target RNA.

Phosphodiester bond cleavage can be accomplished by strategically positioning either proton-accepting, proton-donating, or electron-accepting functional groups, represented by X, Y, and Z respectively, adjacent to such phosphodiester bonds, as shown in Scheme 1, wherein $B_1$ and $B_2$ are nucleoside base units. Additional placement of a proton-donating group, W-H, adjacent to one of the non-ester linkage phosphoryl oxygens may provide additional enhancement of cleavage.

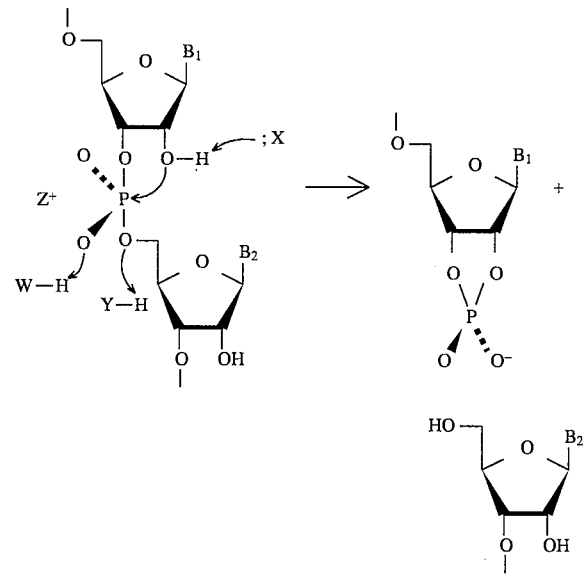

Scheme 1

In some applications, one of the chemical groups may be sufficient to catalyze RNA cleavage. However, in other applications of the invention, the combination of two or even three groups may be preferred. Artisans in the field will have great latitude in selecting the specific reactive functionalities W, X, Y, and/or Z. There is also great latitude in the election to use one or more reactive functionalities in the same molecule.

The present novel approach to obtaining stronger binding and better molecular recognition of cleavage groups with target reactive groups is to prepare antisense RNA mimics to bind to the targeted RNA. Therefore, a structure-activity relationship approach is undertaken to discover nuclease resistant antisense oligonucleotides that maintain appropriate hybridization properties.

A series of 2'-modified nucleosides of adenine, guanine, cytosine, thymidine and certain analogs of these bases are prepared and are inserted as the modified nucleosides into sequence-specific oligonucleotides via solid phase nucleic acid synthesis. The novel antisense oligonucleotides are assayed for their ability to resist degradation by nucleases and to possess hybridization properties comparable to the unmodified parent oligonucleotide. Initially, small electronegative groups are selected because these types are not likely to sterically interfere with required Watson-Crick base pair hydrogen bonding (hybridization). However, electronic changes due to the electronegativity of the atom or group in the 2'-position may profoundly effect the sugar conformation.

The oligonucleotides of this invention can be used in diagnostics, therapeutics, and as research reagents and kits. For therapeutic use, the oligonucleotide is administered to an animal suffering from a disease effected by a protein. Representative antisense approaches to one such disease, papillomavirus infection, are generally provided by U.S. patent application Ser. No. 445,196, filed Dec. 4, 1989, abandoned, the contents of which are incorporated herein by reference.

Oligonucleotides can be formulated in a pharmaceutical composition, which can include carriers, thickeners, diluents, buffers, preservatives, surface active agents and the like in addition to the oligonucleotide. Pharmaceutical compositions also can include one or more active ingredients such as antimicrobial agents, anti-inflammatory agents, anesthetics, and the like in addition to oligonucleotide.

The pharmaceutical composition can be administered in a number of ways depending on whether local or systemic treatment is desired, and on the area to be treated. Administration can be topically (including opthalmically, vaginally, rectally, intranasally), orally, by inhalation, or parenterally, for example by intravenous drip, subcutaneous, intraperitoneal or intramuscular injection.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration can include sterile aqueous solutions which also can contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The following procedures and examples illustrate the practice of this invention. These procedures and examples are not to be construed as limiting the invention.

Once nucleotides of the invention have been prepared, they can then subsequently be incorporated into oligonucleotides of the invention, which are synthesized by a standard solid phase, automated nucleic acid synthesizer such as the Applied Biosystems, Incorporated 380B or MilliGen/Biosearch 7500 or 8800. Triester, phosphoramidite, or hydrogen phosphonate coupling chemistries (see, e.g., M. Caruthers, *Oligonucleotides. Antisense Inhibitors of Gene Expression.*, pp. 7–24, J. S. Cohen, ed., CRC Press, Inc. Boca Raton, Fla., 1989) are used with these synthesizers to provide the desired oligonucleotides. The Beaucage reagent (see, e.g., *J. Am. Chem. Soc.* 1990, 112, 1253) or elemental sulfur (see, e.g., *Tetrahedron Letters* 1981, 22, 1859), is used with phosphoramidite or hydrogen phosphonate chemistries to provide substituted phosphorothioate oligonucleotides.

Fugitive masking groups are used in preparing certain of the compounds of the invention. Such masking groups allow for ease of synthesis of the compounds. The masking groups are subsequently converted to the desired functionality. Such conversion preferably occurs during a standard deblocking step for a later reaction. An example of this procedure is the use of a phthalimide group for the introduction of an amino functionality. Alkyl phthalimides are attached at the proper position in a compound of interest (e.g., a nucleoside) via a suitable intermediate such as an N-(haloalkyl)phthalimide. The derivatized compound is then used in standard oligonucleotide synthetic techniques on a nucleotide synthesizer. After the desired oligonucleotide is prepared, it is cleaved from the synthesizer support using a suitable reagent. The cleaving reagent also converts the alkylphthalimide to the desired alkylamine. Procedures of this type can be expanded to attach longer chain polyamino functionalities to the oligonucleotides of the invention. Nucleotides or oligonucleotides having a first alkylamino functionality are treated with a further N-(haloalkyl) phthalimide. The extended functionality then is treated to yield a terminal amine group. This can be repeated to further extend the polyamino functionality. Alternately, the extended polyamino functionality first is synthesized and reacted with the first alkylamino functionality to form the polyamino functionality.

In one representative preparative example, shown in FIG. 1, adenosine was alkylated with propargyl bromide to give a mixture of the 2'- and 3'-regioisomers, 2 and 3, respectively. This mixture was not resolved but was treated with 1,3-dichlorotetraisopropyl disiloxane to afford the tetraisopropyl disiloxane (TPDS) derivatives. Purification at this stage yielded the novel 2'-propargyl protected nucleoside 4 in 54% yield from adenosine. Deprotection of 4 with nBu$_4$NH$_4$F provided the novel 2'-propargyl nucleoside of adenosine 2 in 90% yield. The TPDS-protected form of 3'-regioisomer 3 also can be separated from 4 and deprotected with nBu$_4$NH$_4$F to provide the novel nucleoside 3. A palladium catalyzed cross-coupling reaction of alkyne 4 and naphthyl triflate 5 furnished coupled nucleoside product 6 in 83% yield. Coupling of alkyne 4 and naphthyl ditriflate 7 provided the naphthyltriflate coupled nucleoside product 8 in 86% yield. Compound 8 was reacted by a Stille-type palladium-catalyzed coupling with imidazole organostannane 9 to afford the imidazoylnaphthyl coupled nucleoside 10 in 48% yield. Treatment of 10 with nBu$_4$NH$_4$F to provide unprotected imidazoylnaphthyl nucleoside 11, followed by selective hydrogenation with Lindlar catalyst, gives cis olefin derivative 12. The trans olefin 13 can also be afforded via selective hydrogenation of 11 with dihydrido(bicarbonato)bis(triisopropylphosphine)rhodium (III). Further hydrogenation of 11, 12 or 13 with palladium will provide alkyl-tethered imidazoylnaphthyl nucleoside 14.

As shown in FIG. 2, the aminopropynyl naphthyl-tethered nucleoside 15 is prepared by effecting a palladium catalyzed coupling of 8 with propargylamine and a carbodiimide mediated condensation of 15 with the protected bis-aminopropyl imidazoyl glycolic acid 16. This affords bis-imidazoyl functionalized nucleoside 17. Stereoselective reduction of 17 as described for 10 will provide cis, cis- and trans, transderivatives, 18 and 19, respectively. Further reduction of 17, 18, or 19 will afford alkyl-tethered bis-imidazolyl-functionalized nucleoside 20.

Figure 3:
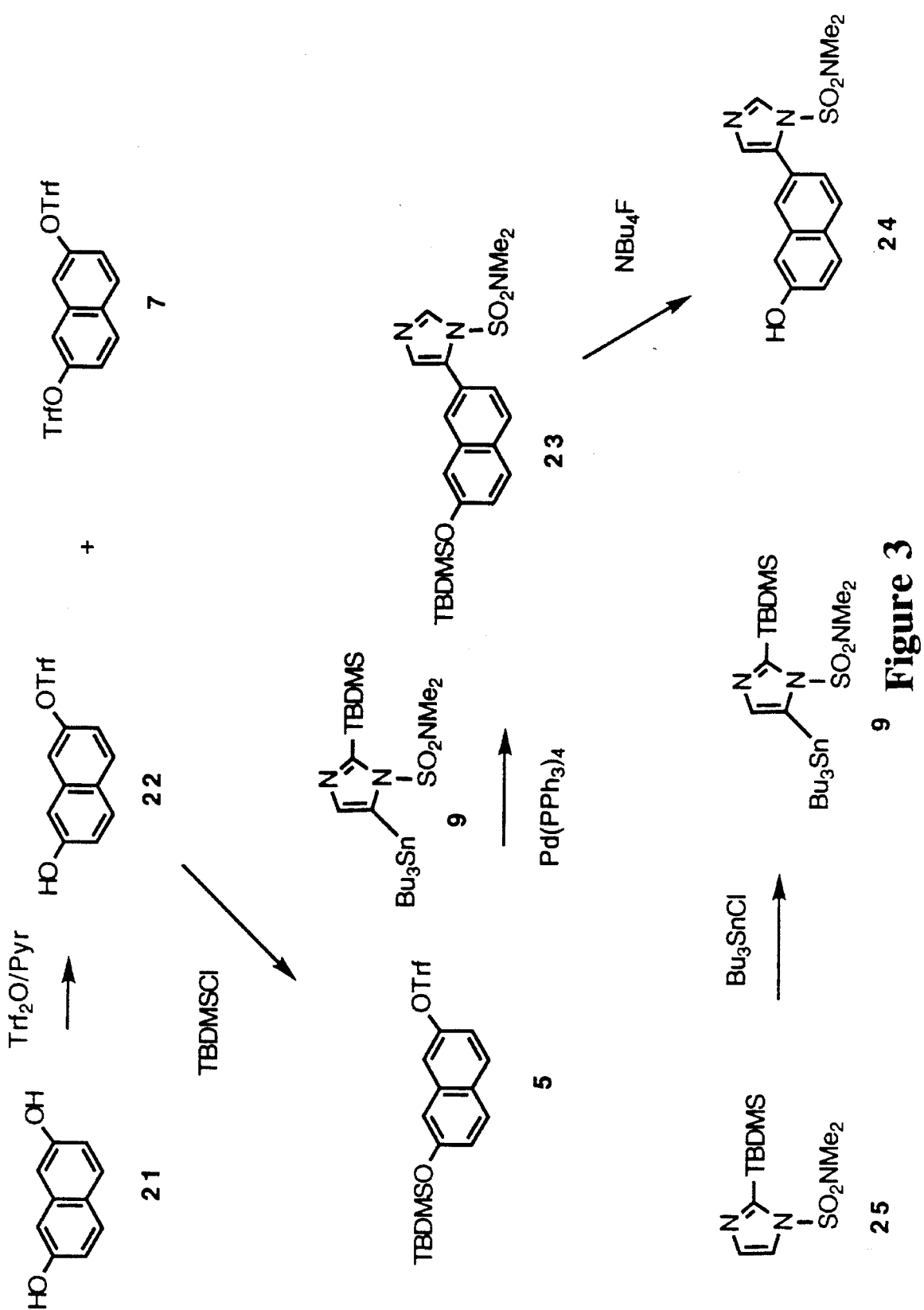
FIG. 3 provides general synthetic schemes for compounds 9 and 24.

The novel compound 7-hydroxy-2-O-triflyl naphthalene 22 was synthesized, as in FIG. 3, in 34% yield by treatment of the naphthalenediol 21 with trifluoromethanesulfonic anhydride. The 2,7-di-O-triflyl naphthalene 7 was afforded concomitantly in 26% yield. Compound 22 was protected with t-butyldimethysilyl to provide 5 in 73% yield. Palladium catalyzed coupling of 5 and organostannylimidazole 9 provided novel protected imidazoylnaphthalene derivative 23 in 38% yield. Deprotection of the t-butyldimethysilyl group gave the novel imidazoylnaphthalene compound 24 in 76% yield. The protected novel organostannylimidazole 9 was prepared by treatment of the reported protected imidazole 25 with tri-n-butyltin chloride to furnish 9 in 52% yield.

As shown in FIG. 4, protected bis-imidazoyl carbinol 26 was synthesized in 69% yield according to the literature procedure of Tang, et al., J. Am. Chem. Soc. 1978, 3918, by reaction of 25 with ethyl formate. Protection of the hydroxyl function was effected with benzylchloromethyl ether to afford 27 in 80% yield. The protected bis-aminopropyl imidazoyl glycolic acid 16 is synthesized by reaction of 25 with DMF and butyl lithium to provide 2-aldehydo derivative 28, which is treated with cyanomethyl diethylphosphonate to afford the modified Wittig product 29. Hydrogenation of 29 with $PtO_2$ furnishes the aminopropyl imidazole 30, which is protected with STABASE (1,1,4,4-tetramethyl-1,4-dichlorosilethylene) to give the amino-protected imidazole 31. Reaction of 31 with ethyl N,N-dimethyl oxamate provides the protected bis-aminopropyl imidazoyl glycolic acid 16, which is deprotected to give the bis-aminopropyl imidazoyl glycolic acid 32. The bis-aminopropyl imidazoyl carbinol 34 is afforded by treatment of 31 with ethylformate to give 33. Deprotection provides bis-aminopropylimidzoyl carbinol 34.

NMR spectra were obtained with the following instruments: $^1$H-NMR: Varian Gemini-200 (199.975 MHz), $^{13}$C-NMR: Varian Gemini-200 (50.289 MHz). NMR spectra were recorded using either deuteriochloroform (tetramethylsilane as internal standard) or dimethylsulfoxide-$d_6$ as solvent. The following abbreviations were used to designate the multiplicity of individual signals: s=singlet, d=doublet, t=triplet, q=quartet, ABq=ab quartet, m=multiplet, dd=doublet of doublets, br s=broad singlet. Mass spectra were acquired on a VG 70-SEQ instrument (VG Analytical (Fisons)), using fast atom bombardment ionization (7 kV Xe atoms). Solvent ratios for column chromatography are given as volume/volume. Evaporations of solvents were performed in vacuo (60 torr) at 30° C. unless otherwise specified.

EXAMPLE 1

9-(2-(O-2-propynyloxy)-β-D-ribofuranosyl) adenine, 2.

Compound 4 was dissolved in THF (10 mL) under an argon atmosphere and 1M tetra-n-butylammonium fluoride (3.6 mL, 3.6 mmol) was added to the reaction mixture to give a turbid solution. After stirring the reaction for 3 hours, the solvent was evaporated in vacuo to give an oil which was purified by column chromatography using EtOAc-MeOH, 80:20, as eluent. Title compound 2 was isolated as a white solid (503 mg, 90%) which was crystallized from methanol at reflux temperature to give white crystals. mp 147°–148° C. $^1$H-NMR (200 MHz, Me$_2$SO-d$_6$): 8.36 (s, 1, H8), 8.13 (s, 1, H2), 7.36 (br s, 2, NH), 6.00 (d, 1, H1', J$_{1',2'}$=6.2 Hz), 5.48 (m, 1, 5'OH), 5.35 (d, 1, 3'OH), 4.68 (m, 1, H2'), 4.32 (m, 1, H3'), 4.21 (ABq, 2, OCH$_2$CC, J=15.7 Hz), 3.98 (m, 1, H1'), 3.58 (m, 2, H5'a, H5'b), 3.27 (s, 1, CCH). FTIR (KBr): 2114 cm$^{-1}$ (w, CCH). Anal. Calcd. for C$_{13}$H$_{15}$N$_5$O$_4$: C, 51.14, N, 4.95, N, 22.94. Found: C, 50.98, H, 4.86, N, 22.81.

EXAMPLE 2

9-(2-(O-2-propynyloxy)-3,5-O-tetraisopropyldisiloxanyl-β-D-ribofuranosyl)adenine, 4.

Adenosine (10.7 g, 40.0 mmol) was dissolved in hot anhydrous DMF (200 mL) under an argon atmosphere, the solution was cooled to 5° C., and NaH (1.76 g, 44 mmol) was added as a 60% dispersion in oil. The reaction mixture was stirred at ambient temperature for 30 min after which time propargyl bromide (4.90 mL, 44 mmol) as an 80% solution in toluene was added via syringe. After the reaction mixture was stirred for 24 hours the solvent was evaporated in vacuo (1 torr) at 40° C. to give a gum. This crude mixture was dried in vacuo (1 torr) at ambient temperature for 18 hours, evaporated with anhydrous pyridine twice, then partially dissolved in hot anhydrous pyridine (120 mL). 1,3-Dichlorotetraisopropyl disiloxane (14.35 mL, 45.6 mmol) was added and the reaction mixture was stirred at ambient temperature for 4 hours and the solvent was evaporated in vacuo (1 torr) at 40° C. to give a residue which was suspended in EtOAc (200 mL). The organic phase was washed with brine, separated and dried with MgSO$_4$. Evaporation of the solvent in vacuo gave an oil which was purified by column chromatography using hexane-EtOAc, 25:75, as eluent. The title compound was obtained as a white solid (11.8 g, 54%). $^1$H-NMR (200 MHz, CDCl$_3$): d 8.32 (s, 1, H8), 8.08 (s, 1, H2), 6.03 (s, 1, H1'), 5.69 (br s, 2, NH), 4.86 (dd, 1, H3'), 4.59 (ABq, 2, OCH$_2$CC, J=15.5 Hz), 4.53 (d, 1, H2', J$_{2',3'}$=4.70 Hz), 4.18 (m, 1, H4'), 4.12 (m, 2, H5'$_a$, H5'$_b$), 2.41 (t, 1, CCH, J=2.28 Hz), 1.08 (m, 28, SiCHMe$_2$). FTIR (NaCl): 2118 cm$^{-1}$ (w, CCH). Anal. Calcd. for C$_{25}$H$_{41}$N$_5$O$_5$Si$_2$: C, 54.82, H, 7.55, N, 12.79, Si, 10.22. Found: C, 54.94, H, 7.63, N, 12.67, Si, 10.13.

EXAMPLE 3

2-(7-t-Butyldimethylsilyloxy)naphthyl trifluoromethanesulfonate, 5.

Compound 22 (8.00 g, 27.4 mmol) was dissolved in anhydrous pyridine (120 mL) under an argon atmosphere and t-butyldimethylchlorosilane (5.37 g, 35.6 mmol) was added. The reaction mixture was stirred at ambient temperature for 24 hours, poured into water (120 mL), and extracted with ether (3×120 mL). The organic phase was separated and washed with water (120 mL), aqueous 10% HCl (120 mL), water (120 mL), and brine (120 mL). After separation, the organic phase was dried with MgSO$_4$ and the solvent was evaporated in vacuo to give an oil, which was purified by column chromatography using hexane-EtOAc, 90:10, as eluent. The title compound was obtained as an oil (8.10 g, 73%). $^1$H-NMR (200 MHz, CDCl$_1$): d 7.86 (m, 6, HAr), 1.02 (s, 9, Me$_3$), 0.26 (s, 6, CH$_3$).

EXAMPLE 4

9-((4-(7-(2-O-t-butyldimethylsilyloxy) naphthyl)-O- 2-propynyloxy-)-3,5-O-tetraisopropyldisiloxanyl-β-D-ribofuranosyl))adenine, 6.

Compound 4 (1.052 g, 1.92 mmol), compound 5 (780 mg, 1.92 mmol), tetrakis (triphenylphosphine) palladium(O) (222 mg, 0.192 mmol), CuI (73 mg, 0.384 mmol), and NEt$_3$ (0.54 mL, 3.84 mmol) were stirred in anhydrous DMF (10 mL) under an argon atmosphere at ambient temperature. After 3 hours the solvent was evaporated in vacuo (1 torr) at 40° C. to give an oil which was dissolved in EtOAc. The organic phase was washed with water, dried with MgSO$_4$, and the solvent was evaporated in vacuo to give a foam. The product was purified by column chromatography using hexane-EtOAc, 50:50, to give the title compound 6 as a foam (1.26 g, 83%). $^1$H-NMR (200 MHz, CDCl$_3$): d 8.28 (s, 1, H8), 8.10 (s, 1, H2), 7.72–7.04 (m, 6, HAr), 6.11 (s, 1, H1'), 5.60 (br s, 2, NH), 4.85 (ABq, 2, OCH$_2$CC, J=15.8 Hz), 4.83 (m, 1, H3'), 4.68 (d, 1, H2'), 4.21 (m, 1, H4'), 4.13 (m, 2, H5'a, H5'b), 1.06 (m, 28, SiCHMe$_2$), 1.01 (s, 9, (CH$_3$)$_3$) , 0.24 (s, 6, CH$_3$-Si) . FTIR (NaCl): 2253 cm$^{-1}$ (w, CCH). Anal. Calcd. for C$_{41}$H$_{61}$N$_5$O$_6$Si$_3$: C, 61.23, H, 7.64, N, 8.71. Found: C, 61.04, H, 7.78, N, 8.26.

EXAMPLE 5

2,7-Di-O-trifluoromethanesulfonyl naphthalene (7) and 2-(7-hydroxy)naphthyl trifluoromethanesulfonate, 22.

2,7-Naphthalenediol (15.0 g, 93.6 mmol) was dissolved in anhydrous pyridine (225 mL) under an argon atmosphere, the solution was cooled to −20° C., and trifluoromethanesulfonic anhydride (17.3 mL, 103 mmol) was slowly added via syringe. The reaction mixture was stirred at −20° C. for 8 hours, poured into water (225 mL), and extracted with ether (3×225 mL). The organic phase was separated, washed with aqueous 10% HCl (225 mL), water (225 mL), and brine (225 mL). The organic phase was separated, dried with MgSO$_4$, and the solvent was evaporated to give an oil which was purified by column chromatography using hexanes-EtOAc, 75:25, as eluent to give the title compound 22 as an oil (9.31 g, 34%). $^1$H-NMR (200 MHz, Me$_2$SO-d$_6$): d 10.13 (s, 1, OH), 7.98–7.16 (m, 6, HAr). $^{13}$C-NMR (50 MHz, CDCl$_3$): d 154.9 (C2), 147.8 (C7), 134.9 (C8$_a$), 130.5, 130.0, 127.8 (C4$_a$), 119 (q, CF$_3$, J$_{C,F}$=320 Hz), 119.3, 117.7, 117.0, 109.7. Compound 7 was also obtained as an oil (10.34 g, 26%). $^1$H-NMR (200 MHz, Me$_2$SO-d$_6$): d 8.28 (m, 4, HAr) , 7.70 (m, 2, HAr). $^{13}$C-NMR (50 MHz, Me$_2$SO-d$_6$): 147.8 (C2, C7) , 133.3 (C8$_a$) , 131.8 (C1, C8) , 121.2 (C3, C6), 119.8 (C4, C5), 118.3 (q, CF, J$_{C,F}$=318 Hz), 115.1 (C4$_a$). Anal. calc. for C$_{12}$H$_6$O$_2$F$_6$: C, 33.97, H, 1.42, S, 15.11, F, 26.87. Found: C, 34.00, H, 1.36, S, 15.11, F, 26.81.

EXAMPLE 6

9-((4-(7-(2-O-trifluoromethanesulfonyl)naphthyl)-O- 2-propynyloxy-)-3,5-O-tetraisopropyldisiloxanyl-β-D-ribofuranosyl)) adenine, 8.

Compounds 4 (3.43 g, 6.27 mmol) and 7 (5.32 g, 12.5 mmol) were dissolved in anhydrous DMF (55 mL). Tetrakis(triphenylphosphine)palladium(O) )217 mg, 0.19 mmol), CuI (72 mg, 0.38 mmol), and NEt$_3$ (0.58 mL, 4.1 mmol) were added and the reaction mixture was stirred under an argon atmosphere at ambient temperature for 1 hour. Additional tetrakis (triphenylphosphine) palladium(O) (217 mg, 0.19 mmol), CuI (72 mg, 0.38 mmol) , and NEt$_3$ (0.58 mL, 4.1 mmol) then were added, the reaction mixture was stirred at ambient temperature for another 2 hours, the reaction mixture was cooled to 5° C., and Et$_2$O (55 mL) and water (55 mL) were added. After stirring for 5 min the organic phase was separated, the aqueous phase was extracted with Et$_2$O (2×50 mL), the Et$_2$O extracts were combined, dried with MgSO$_4$, and the solvent was evaporated in vacuo to give an oil. The crude product was purified by column chromatography using hexanes-EtOAc, 50:50, to give the title compound 8 as a foam (4.48 g, 86%). $^1$H-NMR (200 MHz, Me$_2$SO-d$_6$): 8.23 (s, 1, H8), 8.05 (s, 1, H2), 8.16–7.44 (m, 6, HAr), 7.34 (br s, 2, NH), 6.07 (s, 1, H1'), 5.04 (m, 1, H2'), 4.81 (ABq, 2, OCH$_2$CC, J=15.9 Hz), 4.82 (m, 1, H3'), 4.04 (m, 1, H4'), 3.98 (m, 2, H5'$_a$, H5'$_b$), 1.02 (m, 28, TPDS). $^{13}$C-NMR (50 MHz, CDCl$_3$): 155.6, 153.0, 149.0, 147.5, 138.8, 132.8, 131.6, 131.5, 130.4, 129.7, 127.9, 127.6, 121.7, 120.3, 119.0, 118.7 (q, CF, J$_{C,F}$=320 Hz), 88.6, 86.4, 81.4, 80.1, 77.2, 69.6, 59.8, 59.1, 17.0 (CH$_3$) , 12.7 (CH). $^{19}$F-NMR (188 MHz, CDCl$_3$): d 105.6. FTIR (NaCl): 2231 cm$^{-1}$ (w, CCH).

EXAMPLE 7

2-(t-Butyldimethylsilyl)-5-tri-n-butylstannyl-N,N,-dimethyl-imidazole- 1-sulfonamide, 9.

Compound 25 (20.6 g, 71.2 mmol) was dissolved in anhydrous THF (200 mL) under an argon atmosphere. The solution was cooled to −78° C., and 1.6 M nBuLi (49 mL, 78.4 mmol) was added. After stirring the reaction mixture for 25 min at −78° C., tributyltin chloride (21.26 mL, 78.4 mmol) was added via syringe and the mixture was allowed to warm to ambient temperature. After stirring at ambient temperature for 2 hours, the reaction mixture was poured into ice water (200 mL). Ether (200 mL) was added and the mixture was stirred. The organic phase was separated, dried with MgSO$_4$, and the solvent was evaporated to give an oil which was purified by column chromatography using hexanes followed by hexanes-EtOAc, 90:10, to give the title compound 9 as an oil (21.21 g, 52%). The product was protected from light and stored at 0° C. $^1$H-NMR (200 MHz, CDCl$_3$): d 7.16 (1, s, H4), 2.68 (s, 6, NCH$_3$), 1.5–0.8 (m, Bu), 0.94 (s, 9, Me$_3$), 0.40 (s, 6, SiCH$_3$).

EXAMPLE 8

9-((4-(7-(5-N,N,-dimethylimidazole-1-sulfonamide)naphthyl)-O-2-propynyloxy-)-3,5-O-tetraisopropyldisiloxanyl-β-D-ribofuranosyl))adenine, 10.

Compound 8 (1.00 g, 1.21 mmol), compound 9 (777 mg, 1.34 mmol) , LiCl (149 mg, 3.51 mmol), tetrakis(triphenylphosphine)palladium(O) (140 mg, 0.12 mmol) and 2,6-di-t-butyl- 4-methylphenol (few crystals) were mixed in anhydrous methoxyethyl ether (10 mL) , and the reaction mixture was heated at 120° C. for 2 hours under an argon atmosphere. The reaction mixture was cooled to ambient temperature, Et$_2$O (10 mL) and water (10 mL) were added, and the mixture was stirred for several min. The organic phase was separated, the aqueous phase was extracted with Et$_2$O (2×10 mL) , and the Et$_2$O extracts were combined and dried with MgSO$_4$. The solvent was evaporated in vacuo to give an oil which was purified by column chromatography using EtOAc to afford the title compound as a foam (473 mg, 48%). $^1$H-NMR (200 MHz, CDCl$_3$): 8.25 (s, 1, H8), 8.15 (s, 1, H2) , 8.11 (s, 1, H2-Im), 7.90–7.44 (m, 8, HAr) , 7.15 (s, 1, H4-Im) , 6.34 (br s, 2, NH) , 6.12 (s, 1, H1'), 4.88 (ABq, 2, OCH$_2$CC, J=16 Hz), 4.82 (d, 1, H2'), 4.68 (d, 1, H3', J$_{2',3}$=4.5 Hz) , 4.23 (m, 1, H4') , 4.15 (m, 2, H5'a, H5'b) , 2.43 (s, 6, NCH$_3$) , 1.07 (m, 28, TPDS) . $^{13}$C-NMR (50 MHz, CDCl$_3$): 155.1 (C6, 152.3 (C2), 149.0 (C4), 140.3, 139.0 (C8, C2-Im) , 132.5, 132.0, 131.8, 131.6, 131.4, 129.6, 129.4, 128.8, 127.7, 127.5, 126.4, 120.6, 120.2 (C5, C5-Im) , 88.6 (C1'), 87.0 (CC), 85.6 (CC), 81.4 (C4'), 80.0 (C3'), 69.6 (C2') 59.7, 59.1 (C5', OCH$_2$CC) 37 4 (NCH$_3$), 17.0 (m, CMe$_3$), 12.7 (m, SiCH$_3$). FTIR (KBr): 2230 cm$^{-1}$ (w, CC).

EXAMPLE 9

9-((4-(7-(5-N,N,-dimethylimidazole-1-sulfonamide)naphthyl)-O- 2-propynyloxy-)-β-D-ribofuranosyl))adenine, 11.

Compound 10 (1 mmol) is dissolved in THF (5 mL) and 1M nBu$_4$NH$_4$F (3 mL, 3 mmol) added to the reaction mixture. After stirring the reaction mixture for several hours the solvent is evaporated to an oil and the crude product purified by column chromatography to give the title compound 11.

EXAMPLE 10

9-((4-(7-(5-N,N,-dimethylimidazole-1-sulfonamide)naphthyl)-O- 2-cis-propenyloxy-)-β-D-ribofuranosyl))adenine, 12.

Palladium-on calcium carbonate catalyst (1 g) and benzene (30 mL) are placed in a reaction vessel attached to atmospheric pressure hydrogenation apparatus equipped with a side arm. The air in the system is replaced with hydrogen by evacuating the container and refilling with hydrogen three times. The catalyst suspension is stirred until no more gas is absorbed. Compound 11 (1.7 mmol) then is dissolved in benzene (30 mL) and added to the reaction vessel. The mixture is stirred under a hydrogen atmosphere as rapidly as possible until 207 mL (4.9 molar eq) of gas (22° C., 740 torr) are absorbed over about 5 min. The mixture is filtered through a scintered glass funnel, and the catalyst washed with benzene (3×20 mL). The solvent is evaporated in vacuo and the product purified by column chromatography using hexane-EtOAc as eluent to give the title compound 12.

EXAMPLE 11

9-((4-(7-(5-N,N,-dimethylimidazole-1-sulfonamide)naphthyl)-O- 2-trans-propenyloxy-)-β-D-ribofuranosyl))adenine, 13.

Compound 11 (1.06 mmol) is added to a toluene (10 mL) solution of dihydrido(bicarbonato)bis(triisopropylphosphine)rhodium (III) (0.17 g, 0.35 mmol). After the colorless solution turns orange-red and $CO_2$ has evolved, the concentrated residue of the reaction mixture is washed with hexanes-EtOAc. Evaporation of the washes gives an oil which is purified by column chromatography using hexanes-EtOAc as eluent to yield the title compound 13.

EXAMPLE 12

9-((4-(7-(5-N,N,-dimethylimidazole-1-sulfonamide)naphthyl)-O- 2-propyloxy-)-β-D-ribofuranosyl))adenine, 14.

Compound 11 (0.47 mol), 12 (0.47 mol), or 13 (0.47 mol) are dissolved in absolute ethanol (125 mL) in a Parr bottle containing 5% palladium on carbon catalyst (0.2 g). The bottle is attached to Parr hydrogenation apparatus, and shaken at an initial pressure of 60 psi. After 2 hours hydrogen uptake ceases. The mixture is gravity-filtered twice and the solvent evaporated in vacuo to give an oil which is purified by column chromatography using hexanes-EtOAc as eluent to afford the title compound 14.

EXAMPLE 13

9-((4-(7-(2-(3-Amino-1-propynyl)naphthyl)-O-2-propynyloxy-)- 3,5-O-tetraisopropyldisiloxanyl-β-D-ribofuranosyl))adenine, 15.

Propargyl amine (1.92 mmol), compound 8 (1.92 mmol), tetrakis(triphenylphosphine)palladium(O) (222 mg, 0.192 mmol), CuI (73 mg, 0.384 mmol), and $NEt_3$ (0.54 mL, 3.84 mmol) are stirred in anhydrous DMF (10 mL) under an argon atmosphere at ambient temperature. After 3 hours, the solvent is evaporated in vacuo (1 torr) at 40° C. to give an oil which is dissolved in EtOAc. The organic phase is washed with water and dried with $MgSO_4$. The solvent is evaporated in vacuo to give a foam and the product is purified by column chromatography using hexane-EtOAc to give the title compound 15.

EXAMPLE 14

Bis[4-(2-(t-Butyldimethylsilyl)-5-(3-(N,N- 1,1,4,4-tetramethylsilethylene)aminopropyl)-N,N,-dimethylimidazole-1-sulfonamide)] glycolic acid, 16.

Compound 31 (23 mmol) is dissolved in anhydrous THF (200 mL) and the reaction mixture cooled to −78° C. under an argon atmosphere. nBuLi (1M, 25 mL, 25 mmol) is added and the reaction mixture stirred for 20 min at −78° C. Ethyl N,N-dimethyl oxamate (11.5 mmol) is added and the reaction mixture allowed to slowly warm to ambient temperature. Water (100 mL) and then $Et_2O$ (200 mL) are added. The organic phase is separated and evaporated in vacuo to give the product, which is purified by column chromatography to provide the title compound 16.

EXAMPLE 15

9-((4-(7-(2-(3-N-(bis-[(4-(3-aminopropyl))-5-imidazoyl glycolic acid amide)-1-propynyl)naphthyl)-O-2-propynyloxy-)- 3,5-O-tetraisopropyldisiloxanyl-β-D-ribofuranosyl))adenine, 17.

Compound 16 (1 mmol) is dissolved in anhydrous DMF (5 mL) and dicyclohexylcarbodiimide (1.1 mmol), and N-hydroxybenzotriazole-monohydrate (1.1 mmol) are added. The mixture is stirred under an argon atmosphere for 10 min. Compound 15 then is added, the reaction mixture stirred at ambient temperature for several hours, and water (5 mL) is added. After stirring for 5 min ether (10 mL) is added, the mixture is stirred, the organic phase separated and dried with $MgSO_4$. The solvent is evaporated to give a crude product which is purified by column chromatography using hexanes-EtOAc as eluent to afford the title compound 17.

EXAMPLE 16

9-((4-(7-(2-(3-N-(bis-[(4-(3-aminopropyl))-5-imidazoyl glycolic acid amide)-1-cis-propenyl)naphthyl)-O-2-cis-propenyloxy-)- 3,5-O-tetraisopropyldisiloxanyl-β-D-ribofuranosyl))adenine, 18.

Palladium-on-calcium carbonate catalyst (1 g) and benzene (30 mL) are placed in a reaction vessel attached to an atmospheric pressure hydrogenation apparatus equipped with a side arm. The air in the system is replaced with hydrogen by evacuating the container and refilling with hydrogen three times. The catalyst suspension is stirred until no more gas is absorbed. Compound 17 (1.7 mmol) is dissolved in benzene (30 mL) and the solution added to the reaction vessel. The mixture is stirred under a hydrogen atmosphere as rapidly as possible until 207 mL (4.9 molar eq) of gas (22° C., 740 torr) are absorbed over about 5 min. The mixture is filtered through a scintered glass funnel, and the catalyst washed with benzene (3×20 mL). The solvent is evaporated in vacuo and the product purified by column chromatography using hexane-EtOAc as eluent to give the title compound 18.

EXAMPLE 17

9-((4-(7-(2-(3-N-(bis-[(4-(3-aminopropyl))-5-imidazoyl glycolic acid amide)-1-trans-propenyl)naphthyl)-O-2-transpropenyloxy)-3,5-O-tetraisopropyldisiloxanyl-β-D-ribofuranosyl))adenine, 19.

Compound 17 (1.06 mmol) is added to a toluene (10 mL) solution of dihydrido(bicarbonato)bis(triisopropylphosphine)rhodium (III) (0.17 g, 0.35 mmol). After the colorless solution turns orange-red and $CO_2$ gas has evolved, the concentrated residue of the reaction mixture is washed with hexanes-EtOAc. Evaporation of the washes gives an oil which is purified by column chromatography using hexanes-EtOAc as eluent to yield the title compound 19.

EXAMPLE 18

9-((4-(7-(2-(3-N-(bis-[(4-(3-aminopropyl))-5-imidazoyl glycolic acid amide)-1-propyl)naphthyl)-O-2-propyloxy-)- 3,5-O-tetraisopropyldisiloxanyl-β-D-ribofuranosyl))adenine, 20.

Compound 17 (0.47 mol), 18 (0.47 mol), or 19 (0.47 mol) is dissolved in absolute ethanol (125 mL) in a Parr bottle containing 5% palladium on carbon catalyst (0.2 g). The bottle is attached to a Parr hydrogenation apparatus, and shaken at an initial pressure of 60 psi. After 2 hours, hydrogen uptake ceases and the mixture is gravity-filtered twice. The solvent is evaporated in vacuo to give an oil which is purified by column chromatography using hexanes-EtOAc as eluent to afford the title compound 20.

EXAMPLE 19

7-(5-(2-(t-Butyldimethylsilyl)-N,N,-dimethylimidazole-1-sulfonamide))naphthalene, 23.

Compound 5 (12.65 g, 31.1 mmol), compound 9 (14.5 g, 25.2 mmol), LiCl (3.83 g, 90.2 mmol), tetrakis(triphenylphosphine)palladium(O) (3.60 g, 3.11 mmol) and 2,6-di-t-butyl-4-methylphenol (about 2 mg) were mixed in anhydrous methoxyethylether (130 mL) and the reaction mixture heated at 120° C. for 24 hours under an argon atmosphere. After cooling to ambient temperature pyridine (15 mL) was added, followed by addition of 1.4 M hydrogen fluoride-pyridine in THF (26 mL, 36.4 mmol). After stirring for 5 hours ether (500 mL) was added, the mixture was filtered through Celite and the organic phase was washed with water (500 mL), aqueous 10% HCl (500 mL), water (500 mL), and brine (500 mL). The organic phase was separated, dried with $MgSO_4$, and the solvent was evaporated to give an oil which was purified by column chromatography using hexane-EtOAc, 60:40. The title compound was obtained as an oil (4.15 g, 38%). $^1$H-NMR (200 MHz, $Me_2SO-d_6$): d 8.09 (s, 1, ImH2), 7.84–7.15 (m, 6, HAr), 7.12 (s, 1, ImH2), 2.42 (s, 6, $NCH_3$), 1.02 (s, 9, $Me_3$), 0.26 ($SiCH_3$). $^{13}$C-NMR (50 MHz, $CDCl_3$): d 154.2 (C2), 140.2, 134.0 (C7), 132.2 ($C8_a$), 131.1, 129.3, 129.0 ($C4_a$), 128.7, 127.7, 127.5, 125.9 (2, ImC5), 123.2, 115.1 (ImC4), 37.4 ($NCH_3$), 25.7 ($Me_3$), 18.2 (SiC), −4.3 ($SiCH_3$). Anal. Calc. for $C_{21}H_{29}N_3O_3SSi$: C, 58.44, H, 6.77, N, 9.74, Si, 6.51, S, 7.43. Found: C, 58.22, H, 6.78, N, 9.42, S, 7.44, Si, 6.47.

EXAMPLE 20

2-Hydroxy-7-(5-N,N,-dimethylimidazole-1-sulfonamide)naphthalene, 24.

Compound 23 (4.15 g, 9.61 mmol) was deprotected employing methodology similar to that used for the synthesis of compound 2. A crude oil was obtained which was purified by column chromatography using EtOAc followed by EtOAc-MeOH, 80:20, to afford the title compound 24 as an oil (2.32 g, 76%). $^1$H-NMR (200 MHz, $Me_2SO-d_6$): d 9.83 (s, 1, OH), 8.21 (s, 1, ImH2), 7.84–7.11 (m, 6, HAr), 7.15 (s, 1, ImH4), 2.49 (s, 6, $NCH_3$). $^{13}$C-NMR (50 MHz, $CDCl_3$): d 154.6 (C7), 138.2 (ImC2), 132.5 (C2), 130.7 (C8a), 129.3, 127.6, 126.6, 126.2 (C4a), 125.8, 124.2 (ImC5), 123.2, 118.3, 107.7, 35.8 ($NCH_3$). Anal. calc. for $C_{15}H_{15}N_3O_3S$: C, 56.77, H, 4.76, N, 13.24. Found: C, 56.38, H, 4.88, N, 12.77.

EXAMPLE 21

Bis[5-(2-(t-butyldimethylsilyl)-N,N,-dimethylimidazole-1-sulfonamide)]carbinol, 26.

Compound 25 (14.81 g, 51.2 mmol) was dissolved in anhydrous THF (530 mL) under an argon atmosphere, the solution was cooled to −78° C. and 1.6 M nBuLi (38.4 mL, 61.4 mmol) was added slowly via syringe. After stirring the reaction mixture at −78° C. for 25 min, ethylformate (2.07 mL, 25.6 mmol) was added, and the mixture was allowed to warm to ambient temperature. After stirring for 1 hour, glacial AcOH was added to pH 5, and the mixture was poured into aqueous saturated $NaHCO_3$ (530 mL). The organic phase was separated and the aqueous phase extracted with ether (3×530 mL). The extracts were combined and dried with $MgSO_4$ and the solvent was evaporated in vacuo to give an oil which was purified by column chromatography using $CH_2Cl_2$-acetone, 90:10, to afford the title compound 26 as a solid (10.65 g, 69%). $^1$H-NMR (200 MHz, $CDCl_3$): d 7.04 (s, 2, H4), 6.51 (d, 1, CH, $J_{H,OH}$=3.3 Hz), 3.79 (d, 1, OH), 2.78 (s, 12, $NCH_3$), 0.98 (s, 18, $Me_3$), 0.39 (s, 12, $CH_3$). $^{13}$C-NMR (50 MHz, $CDCl_3$): d 156.9 (C2), 134.8 (C5), 132.2 (C4), 59.6 (COH), 37.7 ($NCH_3$), 27.2 ($Me_3$), 18.3 (SiC), −3.6 ($SiMe_2$). Anal. calc. for $C_{23}H_{46}N_6O_3S_2Si_2$: C, 45.52, H, 7.64, N, 13.85, S, 10.57, Si, 9.26. Found: C, 45.32, H, 7.69, N, 13.93, S, 10.79, Si, 9.30.

EXAMPLE 22

Bis[5-(2-(t-butyldimethylsilyl)-N,N,-dimethylimidazole-1-sulfonamide)]-O-benzyloxymethylcarbinol, 27.

Compound 26 (1.214 g, 2.0 mmol) was dissolved in anhydrous DMF (12 mL), NaH (96 mg, 2.4 mmol) as a 60% dispersion in oil was added at ambient temperature and the reaction mixture was stirred for 10 min under an argon atmosphere. Benzylchloromethyl ether (0.34 mL, 2.2 mmol) then was added. After 4 hours glacial AcOH was added to reach a pH 3, MeOH (2 mL) was added, and the mixture was stirred for 5 min. The solvent was evaporated in vacuo to give an oil which was purified by column chromatography using hexanes-EtOAc, 60:40, as eluent to give the title compound 27 as an oil (1.16 g, 80%). $^1$H-NMR (200 MHz, $CDCl_3$): d 7.33–7.17 (m, 5, HAr), 7.12 (s, 2, ImH4), 6.44 (s, 1, CHO), 4.94 (s, 2, $OCH_2O$), 4.55 (s, 2, $OCH_2Ph$), 2.71 (s, 12, $NCH_3$), 0.98 (s, 18, $Me_3$), 0.40 (s, 6, $SiCH_3$), 0.38 (s, 6, $SiCH_3$).

EXAMPLE 23

2-(t-Butyldimethylsilyl)-5-aldehydo-N,N,-dimethylimidazole-1-sulfonamide, 28.

Compound 25 (1.0 mmol) is dissolved in anhydrous THF (10 mL), the reaction mixture cooled to −78° C., 1M nBuLi (1.1 mL, 1.1 mmol) added, and the reaction mixture stirred at −78° C. for 30 min under an argon atmosphere. Anhydrous DMF (1.1 mmol) then is added, the reaction mixture is stirred at −78° C. for 20 min then allowed to warm to ambient temperature. Ether (10 mL) and then water (5 mL) are added. The organic phase is separated, dried with $MgSO_4$ and the solvent evaporated in vacuo to give a product which is purified by column chromatography to give the title compound 28.

EXAMPLE 24

2-(t-Butyldimethylsilyl)-5-( 2-cyanoethenyl)-N,N,-dimethylimidazole-1-sulfonamide, 29.

Sodium amide (2.0 g, 51.3 mmol) is added under an argon atmosphere to a solution of diethylcyanomethylphosphonate (8.85 g, 50 mmol) in anhydrous THF (40 mL). The suspension is stirred at ambient temperature for 1 hour. A solution of compound 28 (25 mmol) in anhydrous THF (60 mL) is added to the resulting reaction mixture. The mixture is heated at reflux temperature for 20 hours, cooled to ambient temperature, and water (100 mL) is added. After evaporation of the THF in vacuo, $CH_2Cl_2$ (400 mL) is added to the aqueous suspension. The organic phase is separated and the aqueous phase extracted with $CH_2Cl_2$ (2×50 mL). The organic extracts are combined and washed with water (2×50 mL), dried with $MgSO_4$ and evaporated in vacuo to yield a product which is purified by column chromatography to afford the title compound 29.

EXAMPLE 25

2-(t-Butyldimethylsilyl)-5-( 3-aminopropyl)-N,N,-dimethylimidazole-1-sulfonamide, 30.

Compound 29 (2.1 mmol) is dissolved in absolute ethanol (75 mL) and THF (25 mL). Chloroform (1.5 mL) and platinum oxide (70 mg) are added and the mixture subjected to hydrogenation at 5 atmospheres in a Parr hydrogenation apparatus. After 4 hours the mixture is filtered through celite and the celite bed washed with absolute ethanol (2× 20 mL). The filtrate and washings are evaporated in vacuo to give a product which is purified by column chromatography to provide the title compound 30.

EXAMPLE 26

2-(t-Butyldimethylsilyl)-5-(3-(N,N- 1,1,4,4-tetramethylsilethylene)aminopropyl)-N,N,-dimethylimidazole- 1-sulfonamide, 31.

A solution of 1,1,4,4-tetramethyl-1,4-dichlorosilethylene (1.8 g, 8 mmol) in anhydrous $CH_2Cl_2$ (3 mL) is added to a stirred solution of 30 (8 mmol) in $CH_2Cl_2$ (5 mL) containing $NEt_3$ (16 mmol). The mixture is stirred under argon atmosphere at ambient temperature for 2 hours and poured into aqueous sodium dihydrogen phosphate (5 mL). $Et_2O$ (10 mL) then is added. The organic phase is separated and the solvent evaporated in vacuo to give a product which is purified by column chromatography using neutral alumina to provide the title compound 31.

EXAMPLE 27

Bis[4-(5-(3-aminopropyl)-N,N,-dimethylimidazole-1-sulfonamide)] glycolic acid dihydrochloride, 32.

Compound 16 (1 g) is dissolved in 70% aqueous ethanol (20 mL) with concentrated HCl (1 mL) and the mixture heated at reflux temperature for 6 hours. The solvent is evaporated in vacuo to give a product that is crystallized from methanol-chloroform to provide the title compound 32 as the dihydrochloride.

EXAMPLE 28

Bis[4-(2-(t-Butyldimethylsilyl)-5-(3-(N,N- 1,1,4,4-tetramethylsilethylene)aminopropyl)-N,N,-dimethylimidazole-1-sulfonamide)]carbinol, 33.

Compound 31 (23 mmol) is dissolved in anhydrous THF (200 mL), the reaction mixture cooled to −78° C. under an argon atmosphere, and 1M nBuLi (25 mL, 25 mmol) added. After the reaction mixture is stirred for 20 min at −78° C., ethyl formate (11.5 mmol) is added and the reaction mixture allowed to slowly warm to ambient temperature. Water (100 mL) and then $Et_2O$ (200 mL) are added. The organic phase is separated and evaporated in vacuo to give a product which is purified by column chromatography to provide the title compound 33.

EXAMPLE 29

Bis[4-(5-(3-aminopropyl)-N,N,-dimethylimidazole- 1-sulfonamide)]carbinol dihydrochloride, 34.

Compound 33 (1 g) is dissolved in 70% aqueous ethanol (20 mL) with concentrated HCl (1 mL) and the mixture heated at reflux temperature for 6 hours. The solvent is evaporated in vacuo to give a product which is crystallized from methanol-chloroform to provide the title compound 34 as the dihydrochloride.

EXAMPLE 30

Blocked base, 5'-O-DMT blocked, 3'-Phosphoramidite Nucleosides

Appropriately blocked phosphoramidites are prepared utilizing standard reaction for blocking the bases, the 5'-hydroxyl group and adding the 3'-phosphoramidite. Standard blockers are utilized for the bases and the standard DMT (dimethoxytrityl) group utilized for 5' hydroxyl blocking. The procedures are described in various places in the literature as for instance in Gait, M. J. (ed.) *Oligonucleotide Synthesis: A Practical Approach* 1984, IRL Press Ltd., Oxford, UK; and Eckstein, F. (ed.) *Oligonucleotides and Analogues, A Practical Approach,* IRL Press Ltd. by Oxford University Press, New York, 1991.

EXAMPLE 31

Antisense Oligonucleotides

Antisense oligonucleotides according to the present invention possessing intercalating RNA cleavers are prepared by inserting, via standard phosphoamidite coupling chemistry (Gait, M. J. (ed.) *Oligonucleotide Synthesis: A Practical Approach* 1984, IRL Press Ltd., Oxford, UK), one or more nucleosides modified with an intercalator-substituted imidazole adduct into an antisense sequence. Automated nucleic acid synthesizers such as the Applied Biosystems, Inc. 380B can be used to provide the desired modified oligonucleotides, followed by purification trityl-on reverse phase HPLC.

EXAMPLE 32

Other Modifications

The length and the nature of the coupler between the 2'-position of the sugar and the 2-position of the substituted naphthalene can be adjusted by employing a variety of available chemistries. The imidazole can be substituted at its 1-, 2-, and 4-positions to adjust the $pK_a$, hydrogen bonding, and nucleophilicity of the resultant compound. The naphthalene-imidazole adduct can be placed on any nucleic acid nucleoside.

EXAMPLE 33

Hybridization Analysis.

A. Evaluation of the thermodynamics of hybridization of modified oligonucleotides.

The ability of the functionalized oligonucleotides of the invention to hybridize to their complementary RNA or DNA sequences is determined by thermal melting analysis. The RNA complement is synthesized from T7 RNA polymerase and a template-promoter of DNA synthesized with an Applied Biosystems, Inc. 380B nucleic acid synthesizer. The RNA species is purified by ion exchange using FPLC (LKB Pharmacia, Inc.) or by denaturing urea-PAGE. Natural antisense oligonucleotides or those containing functionalization at specific locations are added to either the RNA or DNA complement at stoichiometric concentrations to form hybrid duplexes. The absorbance (260 nm) hyperchromicity dependence on temperature upon duplex to random coil transition is monitored using a Gilford Response II spectrophotometer. These measurements are performed in a buffer of 10 mM Na-phosphate, pH 7.4, 0.1 mM EDTA, and NaCl to yield an ionic strength of either 0.1 M or 1.0 M. Data are analyzed by a graphic representation of $1/T_m$ vs $\ln[Ct]$, where [Ct] is the total oligonucleotide concentration. From this analysis the thermodynamic parameters are determined. Based upon the information gained concerning the stability of the duplex or hetero-duplex formed, the placement of modified pyrimidine into oligonucleotides is assessed for its effects on helix stability. Modifications that drastically alter the stability of the hybrid exhibit reductions or enhancements in the free energy (delta G) and decisions concerning their usefulness in antisense oligonucleotides are made.

B. Fidelity of hybridization of modified oligonucleotides

The ability of the modified antisense oligonucleotides of the invention to hybridize with absolute specificity to the targeted mRNA is shown either by thermodynamic analysis (as above) with target sequences of varying sequence or by Northern blot analysis of purified target mRNA in the presence of total cellular RNA. Target mRNA is synthesized from a vector containing the cDNA for the target mRNA located downstream from a T7 RNA polymerase promoter. Synthesized mRNA is electrophoresed in an agarose gel and transferred to a suitable support membrane (i.e. nitrocellulose). The support membrane is blocked and probed using [$^{32}$P]-labeled antisense oligonucleotides. The stringency is determined by replicate blots and washing in either elevated temperatures or decreased ionic strength of the wash buffer. Autoradiography is performed to assess the presence of heteroduplex formation and the autoradiogram quantitated by laser densitometry (LKB Pharmacia, Inc.) or phosphorimaging (Molecular Dynamics, Inc.). Stringency is predetermined for the unmodified antisense oligonucleotides and the conditions used such that only the specifically targeted mRNA is capable of forming a heteroduplex with the 2'-modified oligonucleotide.

EXAMPLE 34

Nuclease Resistance

A. Evaluation of the resistance of modified oligonucleotides to serum and cytoplasmic nucleases.

Natural phosphorothioate and modified oligonucleotides of the invention are assessed for their resistance to serum nucleases by incubation of the oligonucleotides in media containing various concentrations of fetal calf serum or adult human serum. Labeled oligonucleotides are incubated for various times, treated with protease K and then analyzed by gel electrophoresis on 20% polyacrylamide-urea denaturing gels and subsequent autoradiography or phosphor-imaging. Autoradiograms are quantitated by laser densitometry. Based upon the location of the modifications and the known length of the oligonucleotide it is possible to determine the effect of the particular modification on nuclease degradation. For the cytoplasmic nucleases, a HL60 cell line is used. A post-mitochondrial supernatant is prepared by differential centrifugation and the labeled oligonucleotides are incubated in this supernatant for various times. Following the incubation, oligonucleotides are assessed for degradation as outlined above for serum nucleolytic degradation. Autoradiography results are quantitated for comparison of the unmodified—i.e., phosphorothioate—and the modified oligonucleotides.

B. Evaluation of the resistance of modified oligonucleotides to specific endo- and exo-nucleases.

Evaluation of the resistance of natural and 2'-modified oligonucleotides to specific nucleases (i.e., endonucleases, 3',5'-exo-, and 5',3'-exonucleases) is performed to determine the exact effect of the modifications on degradation. Modified oligonucleotides are incubated in defined reaction buffers specific for various selected nucleases. Following treatment of the products with proteinase K, urea is added and analysis on 20% polyacrylamide gels containing urea is done. Gel products are visualized by staining using Stains All (Sigma Chemical Co.). Laser densitometry is used to quantitate the extent of degradation. The effects of the modifications are determined for specific nucleases and compared with the results obtained from the serum and cytoplasmic systems.

EXAMPLE 35

Screening Of Catalytic, RNA Hydrolytic Cleavage Moieties In A Bimolecular Reaction With HIV-1 TAR RNA Full length (59 mer) wt HIV-1 TAR (transactivation response) RNA is utilized. The TAR structure is prepared from an in vitro RNA T7 polymerase transcription off of a PCR-amplified ds DNA template containing the 17-bp T7 primer site and the 59-bp TAR coding sequence. CIP (calf intestinal phosphatase) is used to 5'-dephosphorylate. This is followed by 5'-kinase end labeling with 7000 Ci/mmol [$\gamma^{32}$P]dATP]. The bimolecular screening reaction mixture variables are: [5'$^{32}$P] TAR: 100 pM; Buffer species: typically sodium or potassium phosphate or MOPS; [Buffer]: 10–100 mM (higher if needed to maintain buffering capacity); EDTA: ±@0.1 mM; NaCl: ±about 100 mM; [Cleaver candidate]: 10 μM–50 mM; Exogenous imidazole: ±up to 1.0 mM; $MgCl_2$: ±@2×[Cleaver] or up to 50 mM; $ZnCl_2$: ±about 2× [Cleaver] or up to 50 mM; pH: 6.0, 7.0 and 8.0; Volume: 10–50 μL; Temperature 37° C.; Time 0–≧48 hours. Analysis is conducted via a denaturing sequencing PAGE analysis. At the appropriate time, an equal volume of 10 M urea is added to the reaction mixture. The reaction mixture is mixed and stored at −20° C. until all time points are collected. The samples are heated to 90° C. for 30 seconds and loaded on a pre-run, pre-heated (50°–55° C.) sequencing gel with reference samples. The reference samples are authentic, untreated TAR RNA, limited base (HO$^-$) treatment laddered TAR, enzyme (i.e. RNase T1) limit digest of TAR and mixture of BB (bromophenol blue) and XC (xylene cyanol) tracking dyes. Urea PA sequencing gel is 12% (20:1 Acryl:Bis) & 50% urea. Electrophoresis is conducted at 70–75 W (about 1750–1950 V, depending on characteristics of gel rig) about 50°–55° C. for about 2 hours until the BB and XC tracking dyes are separated from each other by 14 cm. The gels are developed by autoradiography and/or, for better quantitation, by phosphorimager. The sequence position is identified by counting base laddered TAR from the 3'- and/or 5'-ends and by confirmation via the enzyme digest pattern (i.e. T1 preference for single strand G's of the 6 base loop).

EXAMPLE 36

Screening Of Catalytic Antisense Oligonucleotides

An oligonucleotide is purified by HPLC or PAGE to yield a single chromatographic peaks or bands. About 0.1 to 0.2 $A_{260}$ absorbance units of RNA target strand (strands) and cleaver-conjugated complementary antisense DNA strand are utilized. The target and antisense strands are taken up in a 1:1 stoichiometry in component mixes A-C in 0.6 mL sterile, RNase free, silanized, snap cap tubes to a 10.0 μl final total volume.

|  | A | B | C |
|---|---|---|---|
| NaPi | 10 mM | 10 mM | — |
| Tris-HCl | — | — | 10 mM |
| EDTA | 0.1 mM | 0.1 mM | — |
| NaCl | 100 mM | 100 mM | 100 mM |
| Imidazole | — | 1.0M | 1.0M |
| $MgCl_2$ | — | — | 50 mM |

Three sets of these reactions mixtures are utilized. Set 1 has a pH of 6.0, set 2 has a pH of 7.0, and set 3 has a pH of 8.0. Time points are taken for the 18 resulting test mixtures, i.e. 3 reaction mixture variants×3 pH variant mixtures×2 mixtures (experimental & control). Time points are samples from time 0 to 2 weeks. At each point, the experimental [DNA(+)·RNA]heteroduplex is compared to a control [DNA(−)·RNA]heteroduplex. Temperature is maintained at 37° C. in an incubator during the course of the measurements. The results are analyzed by PAGE utilizing a standard vertical gel rig with approximately 19×19 cm plates (silanized or "Pledged") with 1.5 mm spacers and 20 well comb. Gel is 20% (20:1 Acryl:Bis) urea PAG (about 60 ml). The samples are prepared by addition of equal volumes (10 μl) of 10% glycerol. The samples are not denatured. The gels are pre-run, pre-heated to >55° C. and loaded while hot. All mixes are loaded for a single time point on a single 20 lane gel. The gel is run at 350–450 V (50°–60°) until the bromophenol blue dye is approximated even with the top of the bottom buffer tray. The gel is removed from the plates and stained with Stains-All (over night gives darkest staining). The gels are de-stained and laser densitized and/or photographed. The RNA migrates slower than DNA of same length. DNA stains blue and RNA stains purple.

What is claimed is:

1. A compound of the structure:

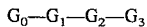

wherein:

$G_0$ is a nucleoside, a nucleotide or an oligonucleotide;

$G_1$ is O—alkyl, O—alkenyl, or O—alkynyl;

$G_2$ is an aryl moiety; and $G_3$ includes at least one imidazole moiety.

2. The compound of claim 1 wherein $G_2$ is a polycyclic moiety having from two to six rings, at least two of said rings being joined to form a conjugated ring system.

3. The compound of claim 2 wherein $G_2$ is an intercalator.

4. The compound of claim 1 wherein $G_2$ is naphthalene, anthracene, phenanthrene, benzonaphthalene, fluorene, or pyrene.

5. The compound of claim 1 wherein $G_3$ is an imidazole; a C2-substituted imidazole; an imidazole substituted at a C4 or C5 position with an electrophilic catalyst; a bis-imidazole; a C2-substituted bis-imidazole; a bis-imidazole wherein at least one C4 or C5 position is substituted with an electrophilic catalyst; a bis-imidazole wherein both C4 positions or both C5 positions are substituted with electrophilic catalyst; or a bis-imidazole wherein the linkage between the imidazole rings is substituted with an electrophilic catalyst.

6. The compound of claim 5 wherein said electrophilic catalyst comprises a nitrogen functionality that can be protonated.

7. The compound of claim 6 wherein said nitrogen functionality is an amine, a nitrogen heterocycle, guanidine or amidine.

8. The compound of claim 1 wherein $G_2$ and $G_3$ are connected through a single covalent bond.

9. The compound of claim 8 wherein $G_3$ includes at least one imidazole moiety covalently bound through a C4 or C5 position.

10. The compound of claim 1 wherein $G_1$ connects to $G_0$ at a 2' sugar position of said $G_0$.

11. A compound of the structure:

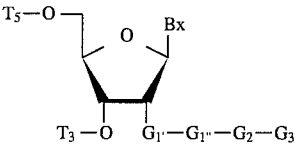

$T_5$ is H, a hydroxyl protecting group, a phosphate group, a nucleotide or an oligonucleotide;

$T_3$ is H, a hydroxyl protecting group, a nucleotide, an oligonucleotide, a phosphate group, an activated phosphate group or solid phase support;

$G_{1'}$ is O;

$G_{1''}$ is alkyl, alkenyl, or alkynyl;

$G_2$ is an aryl moiety;

$G_3$ includes at least one imidazole moiety; and

Bx is a heterocyclic base moiety.

12. The compound of claim 11 wherein $G_2$ is an intercalator.

13. The compound of claim 11 wherein $G_{1''}$ is alkynyl.

14. The compound of claim 11 wherein $G_2$ includes a polycyclic system.

15. The compound of claim 14 wherein said polycyclic system has two to six rings and at least two of said rings are conjugated.

16. The compound of claim 11 wherein $G_2$ is naphthalene, anthracene, phenanthrene, benzonaphthalene, fluorene, or pyrene.

17. The compound of claim 11 wherein $G_3$ is an imidazole moiety.

18. The compound of claim 11 wherein $G_3$ is a bis-imidazole moiety.

19. The compound of claim 11 wherein Bx is a purine heterocyclic base.

20. A compound of the structure:

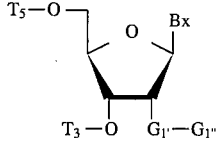

$T_5$ is H, a hydroxyl protecting group, a phosphate group, a nucleotide or an oligonucleotide;

$T_3$ is H, a hydroxyl protecting group, a nucleotide, an oligonucleotide, a phosphate group, an activated phosphate group or a solid phase support;

$G_{1'}$ is O;

$G_{1''}$ is alkynyl; and

Bx is a heterocyclic base moiety, provided that when Bx is uracil then $T_3$ and $T_5$ are not H or acetyl.

21. The compound of claim 20 wherein $G_{1''}$ is propargyl.

* * * * *

UNITED STATES PATENT AND TRADEMARK OFFICE
CERTIFICATE OF CORRECTION

PATENT NO. : 5,514,786  
DATED : May 7, 1996  
INVENTOR(S) : Phillip D. Cook et al Page 1 of 2

Figure 1B:
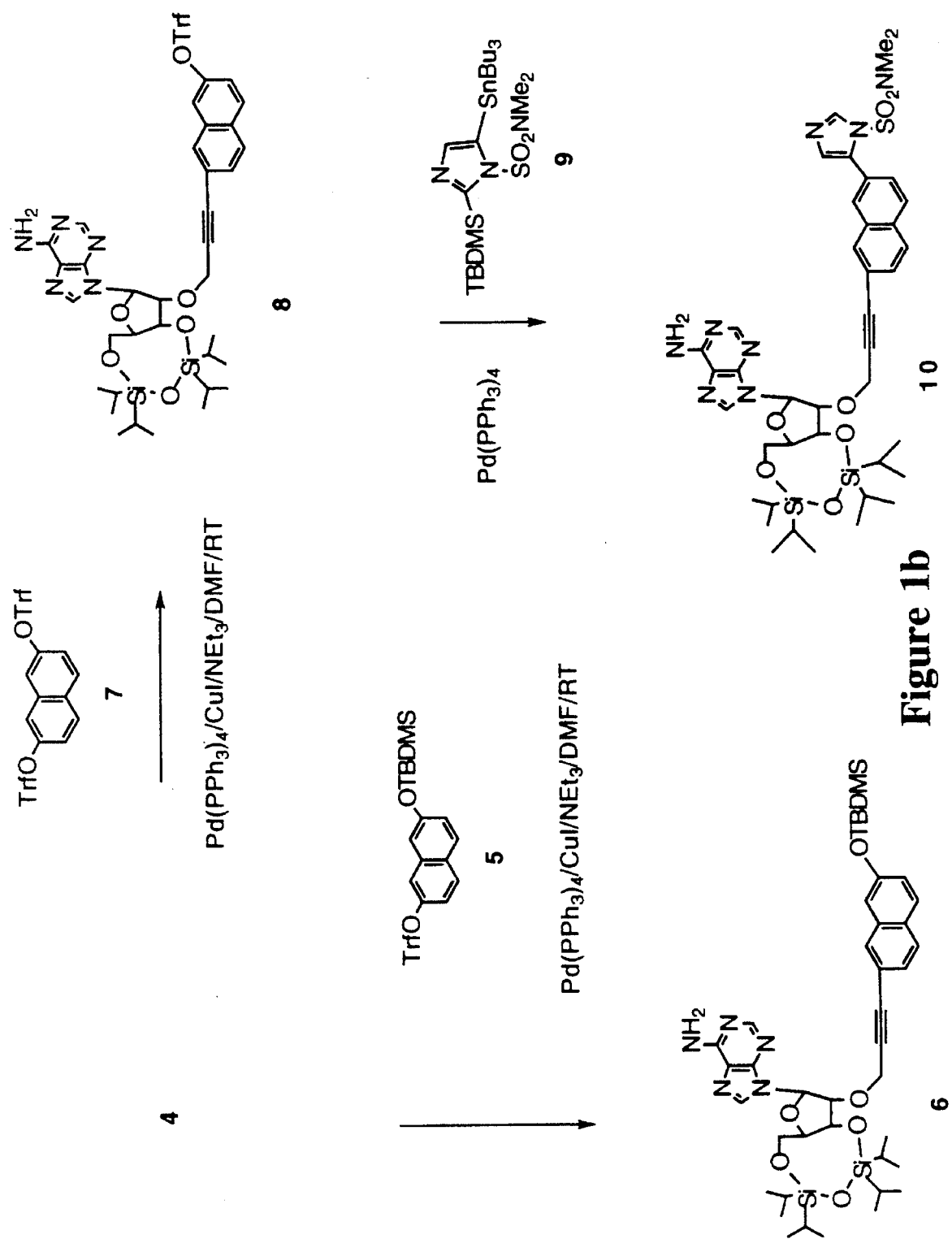
Figure 1C:
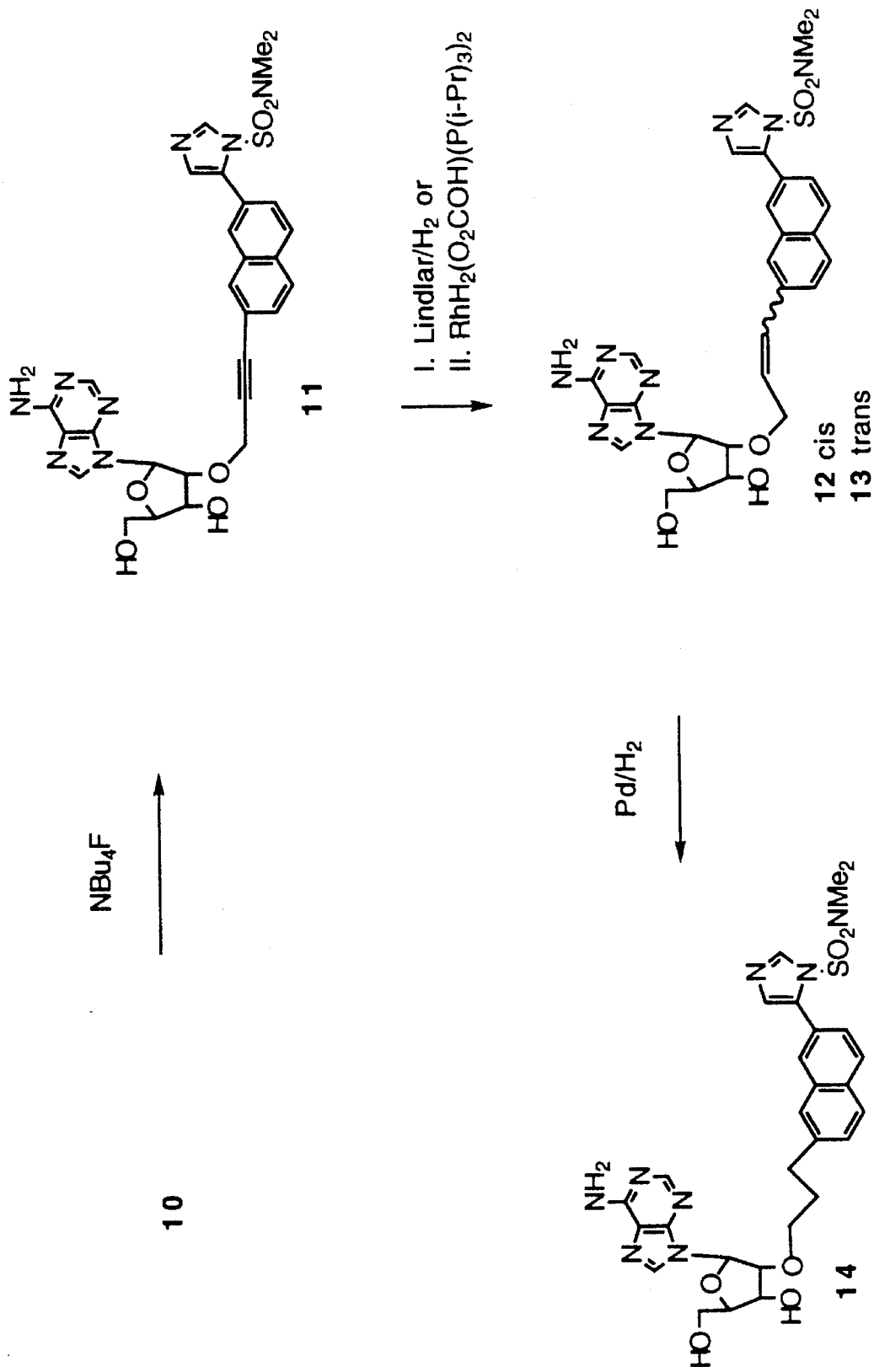

It is certified that error appears in the above-identified patent and that said Letters Patent is hereby corrected as shown below:

Col. 8, line 2, "FIG 1" should be --Figures 1a, 1b, and 1c--; same line "provides" should be --provide--.

Figure 2A:
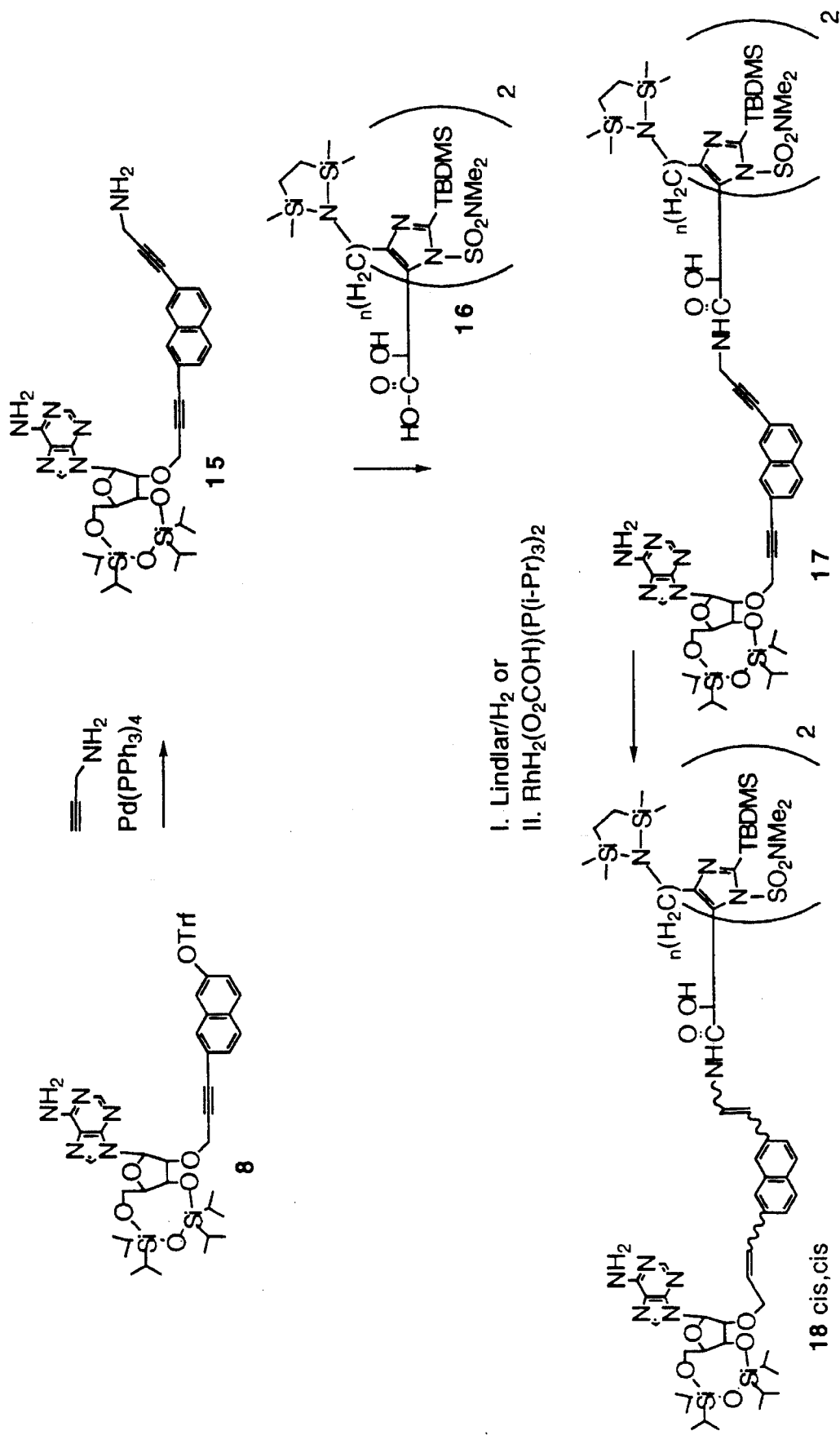
FIG. 2 provides a general synthetic scheme for compound 20.
Figure 2B:
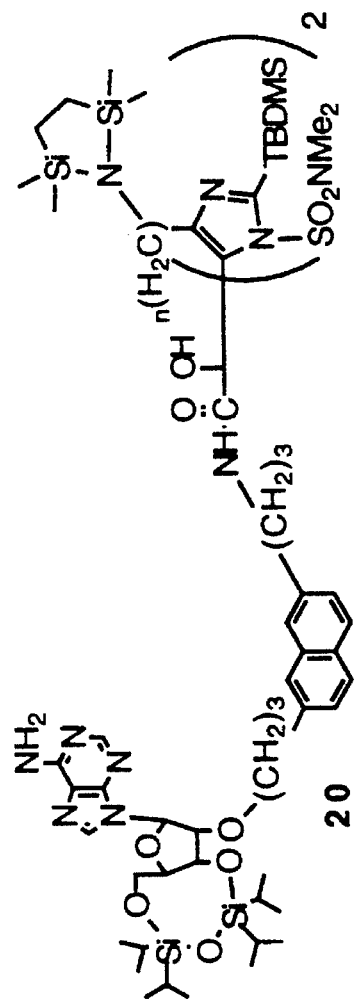

Col. 8, line 4, "FIG. 2" should be --Figures 2a and 2b--; same line, "provides" should be --provide--.

Figure 4A:
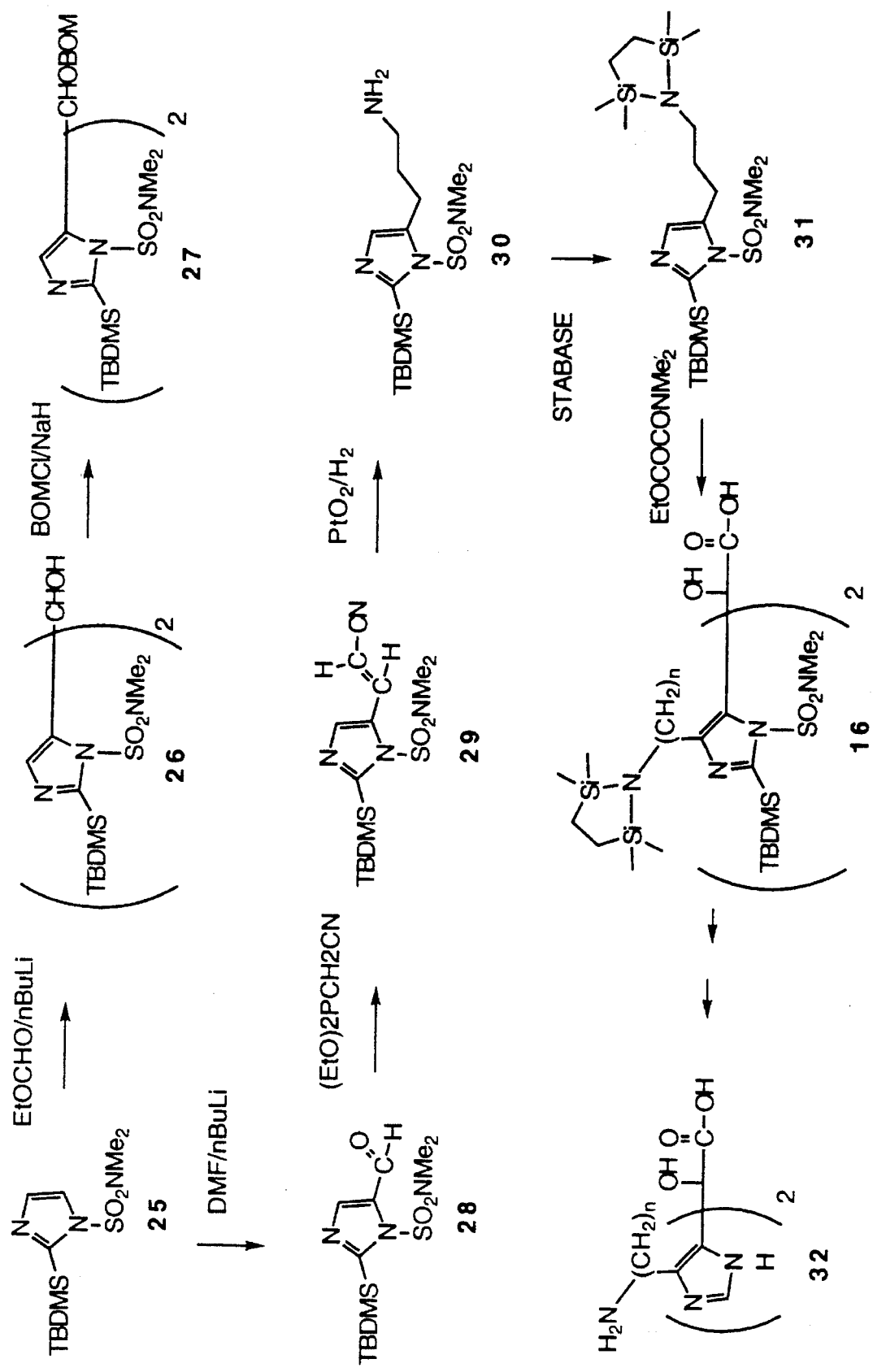
FIG. 4 provides a general synthetic scheme for compound 34.
Figure 4B:
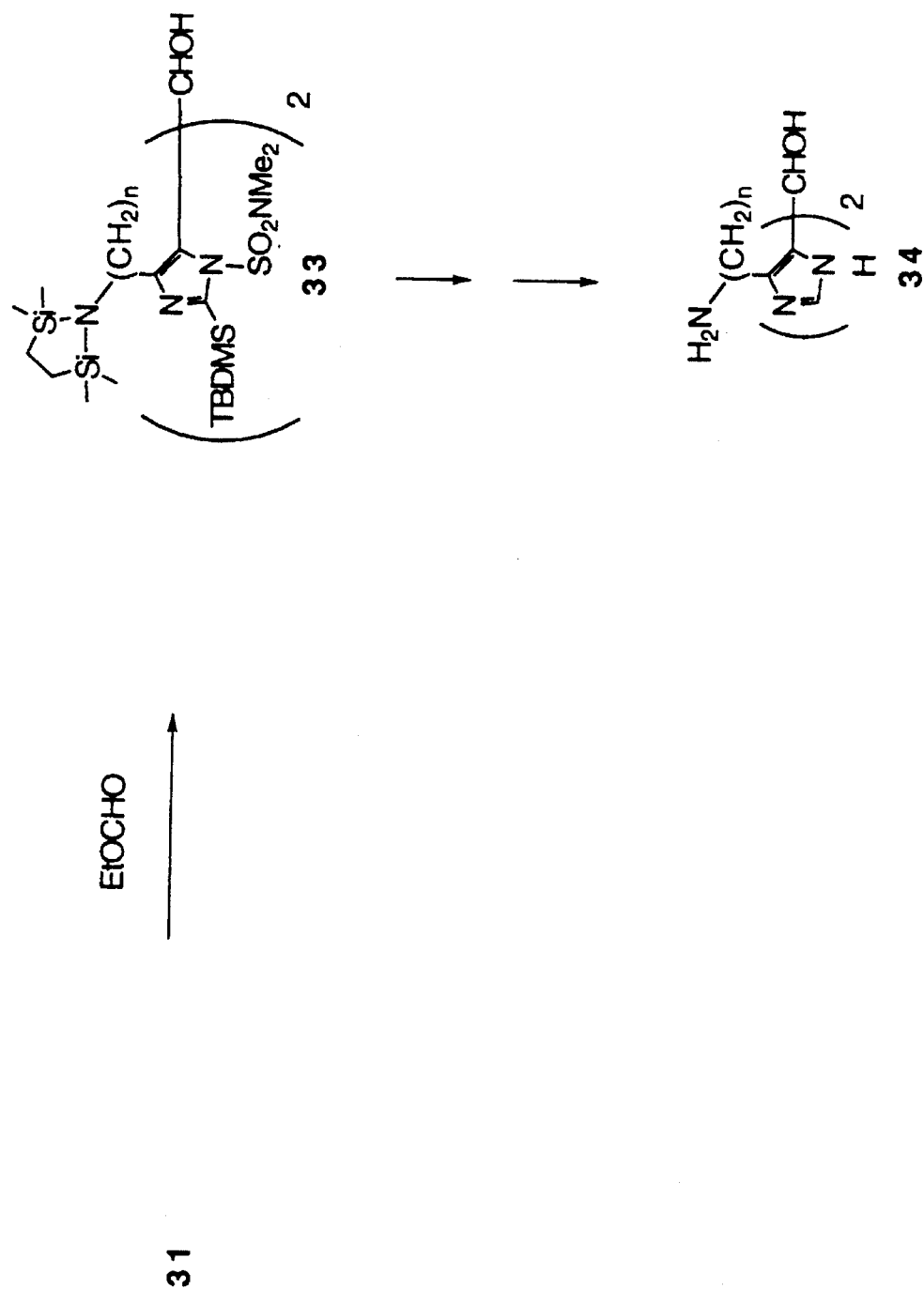

Col. 8, line 8, "FIG. 4" should be --Figures 4a and 4b--; same line, "provides" should be --provide--.

Col. 12, line 28, "GI" should be --$G_1$--.

Col. 22, line 25, "FIG. 1" should be --Figures 1a, 1b and 1c--.

UNITED STATES PATENT AND TRADEMARK OFFICE
CERTIFICATE OF CORRECTION

PATENT NO. : 5,514,786
DATED : May 7, 1996
INVENTOR(S) : Phillip D. Cook et al

It is certified that error appears in the above-identified patent and that said Letters Patent is hereby corrected as shown below:

Col. 22, line 52, "FIG. 2" should be --Figures 2a and 2b--

Col. 23, line 65, "H1" should be --H4'--.

Col. 24, line 50, "CDCl$_1$" should be --CDCl$_3$--.

Col. 25, line 45, delete ")" and insert --(--.

Col. 36, lines 45-63, cancel claims 20 and 21

Signed and Sealed this

Seventh Day of December, 1999

Attest:

Q. TODD DICKINSON

*Attesting Officer*      *Acting Commissioner of Patents and Trademarks*